US011466240B2

(12) United States Patent
Kumacheva et al.

(10) Patent No.: US 11,466,240 B2
(45) Date of Patent: Oct. 11, 2022

(54) MICROFLUIDIC PLATFORM FOR THE RAPID PRODUCTION OF ORGANOIDS/SPHEROIDS FOR COMPOUND SCREENING

(71) Applicant: THE GOVERNING COUNCIL OF THE UNIVERSITY OF TORONTO, Toronto (CA)

(72) Inventors: Eugenia Kumacheva, Toronto (CA); Elisabeth Prince, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 169 days.

(21) Appl. No.: 16/630,965

(22) PCT Filed: Jul. 16, 2018

(86) PCT No.: PCT/CA2018/050862
§ 371 (c)(1),
(2) Date: Jan. 14, 2020

(87) PCT Pub. No.: WO2019/010587
PCT Pub. Date: Jan. 17, 2019

(65) Prior Publication Data
US 2020/0224137 A1 Jul. 16, 2020

Related U.S. Application Data

(60) Provisional application No. 62/532,723, filed on Jul. 14, 2017.

(51) Int. Cl.
*C12M 3/00* (2006.01)
*C12N 5/00* (2006.01)
(Continued)

(52) U.S. Cl.
CPC .......... *C12M 23/16* (2013.01); *B01L 3/5027* (2013.01); *C12M 21/08* (2013.01); *C12M 23/12* (2013.01);
(Continued)

(58) Field of Classification Search
CPC ....... C12M 23/12; C12M 23/16; B01L 3/5027
See application file for complete search history.

(56) References Cited

U.S. PATENT DOCUMENTS

2009/0018033 A1* 1/2009 Morgan ............... C12N 5/0062
435/375
2014/0357511 A1* 12/2014 Handique ......... B01L 3/502761
506/10

FOREIGN PATENT DOCUMENTS

KR 20170071450 A 6/2017
WO 2010023497 A1 3/2010
(Continued)

OTHER PUBLICATIONS

Sabhachandani, P. et al. 2016. Generation and functional assessment of 3D multicellular spheroids in droplet based microfluidics platform. Lab on a Chip 16: 497-505. specif. pp. 497, 500, 501.*
(Continued)

Primary Examiner — Nathan A Bowers
(74) Attorney, Agent, or Firm — Hill & Schumacher

(57) ABSTRACT

The present disclosure provides a method of producing uniformly sized organoids/multicellular spheroids using a microfluidic device having an array of microwells. The method involves several successive steps. First, a microfluidic device containing parallel rows of microwells that are connected with a supplying channel is filled with a wetting agent. The wetting agent is a liquid that is immiscible in water. For example, the wetting agent may be an organic liquid such as oil. In the next step, the agent in the supplying channel and the microwells is replaced with a suspension of
(Continued)

cells in an aqueous solution that contains a precursor for a hydrogel. Next, the aqueous phase in the supplying channel is replaced with the agent, which leads to the formation of an array of droplets of cell suspension in the hydrogel precursor solution, which were compartmentalized in the wells. The droplets are then transformed into cell-laden hydrogels. Subsequently, the agent in the supplying channel is replaced with the cell culture medium continuously flowing through the microfluidic device and the cells within the hydrogels are transformed into multicellular spheroids.

13 Claims, 32 Drawing Sheets

(51) Int. Cl.
| | |
|---|---|
| *C12M 3/06* | (2006.01) |
| *B01L 3/00* | (2006.01) |
| *C12M 1/32* | (2006.01) |
| *C12M 1/00* | (2006.01) |
| *C12M 1/12* | (2006.01) |
| *C12N 5/09* | (2010.01) |
| *G01N 33/50* | (2006.01) |

(52) U.S. Cl.
CPC ............ *C12M 23/20* (2013.01); *C12M 25/14* (2013.01); *C12M 29/00* (2013.01); *C12N 5/0693* (2013.01); *G01N 33/5011* (2013.01); *G01N 33/5032* (2013.01); *B01L 2300/0809* (2013.01); *B01L 2300/12* (2013.01); *C12N 2533/30* (2013.01); *C12N 2533/54* (2013.01); *C12N 2533/56* (2013.01); *C12N 2533/76* (2013.01); *C12N 2533/78* (2013.01); *C12N 2533/80* (2013.01)

(56) References Cited

FOREIGN PATENT DOCUMENTS

| WO | 2015200832 A1 | 12/2015 |
|---|---|---|
| WO | 2016059302 A1 | 4/2016 |

OTHER PUBLICATIONS

Yuan et al, "An automated microwell platform for large-scale single cell RNA-Seq". Scientific Reports, Sep. 27, 2016, vol. 6(33883), pp. 1-10.
Sabhachandani et al., "Generation and functional assessment of 3D multicellular spheroids in droplet based microfluidics platform". Lab on a Chip, Jan. 26, 2016, vol. 16(3), pp. 497-505.
Ieong et al., "Investigation of drug cocktail effects on cancer cell-spheroids using a microfluidic drug-screening assay". Micromachines, May 24, 2017, vol. 8(167), pp. 1-12.
Mcmillan et al, "Transitioning from multi-phase to single-phase microlluidics for long-term culture and treatment ofmulticellular spheroids". Lab on a Chip, Sep. 21, 2016, vol. 16(18), pp. 3548-3557.
Therien-Aubin et al., "Temperature-responsive nanofibrillar hydrogels for cell encapsulation". BioMacromolecules, Sep. 10, 2016, vol. 17(10), pp. 3244-3251.
Nath et el., "Three-dimensional culture systems in cancer research: focus on tumor spheroid model". Pharmacology and Therapeutics, Apr. 8, 2016, vol. 163, pp. 94-108.
International Search Report of parent PCT/CA2018/050862 filed Jan. 14, 2020. The date of the search report is Oct. 25, 2018.
Hui Wen et al. "A droplet microchip with substance exchange capability for the development study of C. elegans" Lab Chip 2015 vol. 15 1905-1911.
Stefania Mazzitelli et al. "Preparation of cell-encapsulation devices in confined microenvironment", Advanced Drug Delivery Reviews 65 (2013) p. 1533-1555.

* cited by examiner

| [a-CNC] | Young's Modulus |
|---|---|
| 0.3 wt% | 1.8± 0.7 kPa |
| 0.5 wt% | 1.9± 0.4 kPa |
| 1.0 wt% | 3.4± 0.8 kPa |
| 1.5 wt% | 4.9± 0.6 kPa |
| 2.0 wt% | 6.8± 0.8 kPa |

FIG. 6

MICROFLUIDIC PLATFORM FOR THE RAPID PRODUCTION OF ORGANOIDS/SPHEROIDS FOR COMPOUND SCREENING

FIELD

The present disclosure relates to a microfluidic (MF) platform for the generation and growth of uniformly sized organoids and/or multicellular spheroids (MCSs) under close-to-physiological flow conditions and the delivery of anticancer drugs to multicellular spheroids for throughput screening of drug efficacy for therapeutic treatment.

BACKGROUND OF THE INVENTION

Cancer remains the leading cause of death worldwide and among Canadians: about 2 in 5 Canadians will be diagnosed with cancer during their lifetime, with half of new cases being prostate, breast, lung and colorectal cancers (1 in 4 will die and 60% diagnosed with cancer will survive at least, 5 years after the diagnosis). For many cancer patients standard-of-care therapy involves surgical removal of the primary tumour. The success of this approach is often unsuccessful due to the growth of secondary tumours at distant sites. Therapies are required that are either directly toxic toward the proliferating metastatic cells, or that lock micrometastases in their dormant state. To eradicate metastasis, chemotherapy is administered after primary surgery, however there is a challenge to assess and predict the effectiveness of drugs for microtumors with dimensions in the range of tens to hundreds of micrometers that are grown in environments with different protective properties.

One of the major hurdles impeding the development of cancer therapeutics (and micrometastases, in particular) is the limitations of current model systems. Conventional models used for anticancer drug screening include in vitro studies conducted in a 2D format (in Petri dishes or well plates) and animal (zenograph) studies. Animal models are expensive, being both labor- and time-consuming. Moreover, animal models generally only provide endpoint analyses, in addition to issues of relevance for the human condition. Typically, immunocompromised murine models are used, however it is established that the immune system is crucial to the micrometastatic microenvironment. Those animal studies that do use syngeneic models (tumor tissues derived from the same genetic background as a given mouse strain) are also not fully representative of the human situation due to differences in cytokines and metabolism.

In vitro culture resolves some of the issues of animal studies, however most of conventional in vitro drug screening is conducted by using 2D culture systems. These systems lack important aspects which impact tumor behavior, such as 3D architecture to provide tissue depth for tumor intercalation, functional aspects, including fluid flow and control of oxygen content, and do not allow for time-extended culture. There is also a distinct absence of systems capable of recreating micrometastasis while concurrently providing for the evaluation of drug efficacy, toxicity and metabolism.

Cells cultured in 2D environments may be capable of forming multi-cell spheroids (MCSs), but these spheroids differ considerably in their properties and phenotype from those grown in physiological 3D environments, and may not serve as an efficient model for drug screening. Organotypical multicellular spheroids-3D aggregates of malignant cells that replicate many features of microtumors—serve as a bridge between 2D cell cultures and animal models to overcome some of the limitations listed above.

Cancer spheroids, namely, dense cancer cell clusters with typical sizes in the range from tens of micrometers to one millimetre, are extensively used as models of solid tumors for fundamental research in cell biology and for clinical applications, e.g., for studies of tumor response to chemo- and radiation therapies. They replicate many features of tumors, e.g., cell-cell adhesion, cell-matrix interactions and gradients in the concentration of nutrients and gases. Cancer spheroids are prepared in several different ways, that is, by partial or complete dissociation of tissues, by growth and proliferation of individual (isolated) cancer cells, or by aggregation of individual cancer cells in dense clusters.

However, existing MCS models currently used for drug screening have at least one of the following limitations:
 (i) broad size distribution which interferes with the efficiency of drug screening;
 (ii) poorly understood role of metastatic niche (microenvironment) on MCS therapeutic treatment;
 (iii) drug delivery under conditions that do not mimic natural continuous flow conditions;
 (iv) low reproducibility and
 (v) lack of throughput screening of drug efficacy.

Another important consideration in the preparation and use of multicellular spheroids as tumorigenic models is the rate of their formation in vitro, which can vary from days to weeks, in order to reach the size of several hundred micrometers. Fast growth of multicellular spheroids in vitro is highly advantageous. Due to the rapid formation and growth, multicellular spheroids formed by aggregation of individual cells from their dense suspensions are particularly useful. Unfortunately, multicellular spheroids generated using this method, are generally formed in the absence of their extracellular matrix (ECM), which is one of the main components of their natural microenvironments, as it provides biophysical and biochemical cues to tumor growth. Although cancer cells in multicellular spheroids generated by cell aggregation can secret ECM components, the composition of these ECMs is complex, thereby making it is difficult to disentangle the effect of each ECM component on the growth and progression of cancer cells. On the other hand, multicellular spheroids formed by the growth of individual isolated cancer cells have been prepared in various ECMs, e.g., Matrigel, fibrin or collagen, however this process is slow and it lacks the physiological flow conditions.

Another important consideration in MCS generation and potential applications is the uniformity in their dimensions. Existing methods used for the generation of multicellular spheroids by cell aggregation, including rotary culture, cell aggregation on a non-adherent or a hanging drop method, yield multicellular spheroids with a broad size distribution. For example, a population of multicellular spheroids can have diameters varying from 200 to 800 μm. The high polydispersity of multicellular spheroids imposes uncertainty in diffusion of drugs to the spheroid center or the effect of hypoxia on MCS fate.

SUMMARY

Microfluidics (MFs) offers a platform for the generation of uniformly-sized multicellular spheroids in high efficiency. In particular, MF systems are advantageous as these devices enable the culture of multicellular spheroids under flow and deliver drugs to multicellular spheroids in flow, which enables close mimicking of natural dynamic conditions for tumor growth and progression, as well as chemotherapy. Microfluidics also offers the capability of multiplexing, that is, the exploration of a variety of different factors and their impact on the contained cells, e.g., MCS size and composition, or the effect of different drugs delivered in different dosages in a single series of experiments conducted on a single MF chip.

Thus, the present disclosure is drawn to a MF-MCS platform for drug screening, which can achieve the growth of large arrays of uniformly sized multicellular spheroids with various dimensions under continuous close-to-physiological flow conditions and the delivery of anticancer drugs to multicellular spheroids under dynamic conditions for throughput screening of drug efficacy for therapeutic treatment.

The advantages of the MF-MCS platform disclosed in the current application include, but are not limited to: the ability for the device to contain a large number of multicellular spheroids along each row (leading to statistically significant results), a large number of parallel MCS rows (enabling screening of a particular factor, e.g., drug dose, combinations of different drugs, or the role of MCS size on drug efficacy), a small number of malignant cells and amount of ECM needed for MCS growth (e.g., primary cells can be taken from a particular cancer patient) and the capability to parallelize several screening processes conducted under close-to-physiological flow conditions.

This particular MF-MCS platform holds great potential for cancer drug screening and in particular, as a predictive tool in the evaluation of the output of adjuvant chemotherapy for individual patients, thus enabling rapid decision making regarding the selection of the treatment strategy for a specific patient. Using this platform, screening of drugs can be achieved with higher accuracy, in a shorter time, and with fewer resources than using conventional drug screening procedures.

The present disclosure provides a method of producing uniformly sized multicellular spheroids using a microfluidic device having an array of microwells. The method involves several successive steps. First, a microfluidic device containing parallel rows of microwells that are connected with a supplying channel is filled with a wetting agent. The wetting agent is a liquid that is immiscible in water. For example, the wetting agent may be an organic liquid such as oil. In the next step, the agent in the supplying channel and the microwells is replaced with a suspension of cells in an aqueous solution that contains a precursor for a hydrogel. Next, the aqueous phase in the supplying channel is replaced with the agent, which leads to the formation of an array of droplets of cell suspension in the hydrogel precursor solution, which were compartmentalized in the wells. The droplets are then transformed into cell-laden hydrogels. Subsequently, the agent in the supplying channel is replaced with the cell culture medium continuously flowing through the microfluidic device and the cells within the hydrogels are transformed into multicellular spheroids.

Thus, the present disclosure provides a method for producing multicellular aggregates, in a microfluidic device comprising at least one row having at least one microwell, for each row, a supplying channel spanning along a length of the row and each microwell is in flow connection with the supplying channel, the method comprising the steps of:

introducing a first wetting agent into the supplying channel and corresponding microwells of at least one row of the microfluidic device; introducing a solution comprising an aqueous suspension of cells and a hydrogel precursor into the supplying channel and corresponding at least one microwell of the at least one row of the microfluidic device to replace the first wetting agent within the supplying channel and the at least one microwell with the solution;

introducing a second wetting agent into the supplying channel of the at least one row of the microfluidic device to replace the solution within the supplying channel with the second wetting agent, wherein replacing the solution in the supplying channel with the second wetting agent induces the formation of droplets containing the aqueous suspension of cells and the hydrogel precursor within the at least one microwell of the at least one row of the microfluidic device;

inducing the gelation of the hydrogel precursor within the droplets to form a hydrogel seeded with the suspension of cells; and introducing a cell culture medium into the supplying channel of the at least one row of the microfluidic device to replace the second wetting agent in the supplying channel.

The method may further comprise the step of continuously flowing the cell culture medium into the supplying channel of the at least one row of the microfluidic device, wherein the cell culture medium promotes cell growth of the suspension of cells and the formation of the multicellular aggregates within the hydrogels.

This step of flowing the cell culture medium into the supplying channel of the at least one row of the microfluidic device promotes the formation of the multicellular aggregates within about 1 to about 3 days.

The first wetting agent and the second wetting agent may be the same.

Each wetting agent may be a fluorinated oil mixture comprising a fluorinated oil and a surfactant. In this respect the surfactant may be a block copolymer perfluorinated polyether-b-(polypropylene glycol-polyethylene glycol-polypropylene glycol)-b-perfluorinated polyether.

The hydrogel precursor may comprise a synthetic monomer or polymer, a biopolymer or a combination thereof.

The hydrogels may be obtained through chemical cross-linking of the hydrogel precursor.

The hydrogel precursor may be a mixture of a flexible polymer precursor containing free amine groups and aldehyde-modified cellulose nanocrystals or fibers.

The hydrogel precursor may be functionalized with growth factors and/or peptide fragments.

The hydrogels may be obtained through physical cross-linking of the hydrogel precursor. In this respect the hydrogel precursor may be functionalized with growth factors and/or peptide fragments. The hydrogel precursor may be agarose.

The gelation of the hydrogels may occur within at least 10 min, about 30 minutes to 1.5 hours or about 1 to about 1.5 hours.

The multicellular aggregates may be multicellular spheroids, and the multicellular spheroids may be obtained with an aqueous suspension of cancer cells.

Alternatively the multicellular aggregates may be organoids, and the aqueous suspension of cells may be an aqueous suspension of breast cancer cells or pancreatic cancer cells.

The multicellular aggregates may have a diameter of at least 40 μm, about 40 μm to 1000 μm, about 50 to 1000 μm, about 100 μm to about 1000 μm or greater than 1000 μm. In this respect the multicellular aggregates may have a diameter ranging from about 50 to 300 μm.

The height of the at least one microwell is larger than a diameter of the at least one microwell. In this respect the height of the at least one microwell is about at least 20% larger than a diameter of the at least one microwell.or about 20% larger than the diameter of the at least one microwell.

The supplying channel may have a height and wherein the height of the at least one microwell is greater than the height of the supplying channel. In this respect, the ratio is at least about 4.5 or between about 4.5 to about 5.5.

The hydrogels containing the multicellular aggregates may have a stiffness ranging between about 10 Pa to hundreds kPa or 50 Pa to about 100 KPa or 10 Pa to about 20 KPa. In this respect, the hydrogels containing the multicellular aggregates have a stiffness ranging between about 50 Pa to about 20 Kpa.

The formation of the multicellular aggregates within the hydrogels may comprise large arrays of uniformly-sized multicellular aggregates having diameters ranging from of at least 40 μm, about 40 μm to 1000 μm, about 50 to 1000 μm, about 100 μm to about 1000 μm or greater than 1000 μm.

The hydrogel precursor may be a hydrogel precursor or a combination of hydrogel precursors of any one of the following hydrogels: collagen, gelatin, fibrin, agarose, alginate, polyacrylamide, polyethylene glycol, hyaluronic acid, cellulose derivatives, polypeptides, and mixtures of these polymers and nanoparticles functionalized with biopolymers or synthetic monomers or polymers.

The at least one microwell may be a plurality of microwells.

The present disclosure provides a method for compound screening with multicellular aggregates in a microfluidic device comprising at least one row having a plurality of microwells, for each row, a supplying channel spanning along a length of the row and each microwell is in flow connection with the supplying channel, the method comprising the steps of:

introducing a first wetting agent into the supplying channel and corresponding microwells of at least one row of the microfluidic device;

introducing a solution comprising an aqueous suspension of cells and an hydrogel precursor into the supplying channel and corresponding microwells of the at least one row of the microfluidic device to replace the first wetting agent within the supplying channel and the microwells with the solution;

introducing a second wetting agent into the supplying channel of the at least one row of the microfluidic device to replace the solution within the supplying channel with the second wetting agent, wherein replacing the solution in the supplying channel with the second wetting agent induces the formation of droplets containing the aqueous suspension of cells and the hydrogel precursor within the microwells of the at least one row of the microfluidic device;

inducing the gelation of the hydrogel precursor within the droplets to form a hydrogel seeded with the suspension of cells;

introducing a cell culture medium into the supplying channel of the at least one row of the microfluidic device to replace the second wetting agent in the supplying channel;

continuously flowing the cell culture medium into the supplying channel of the at least one row of the microfluidic device, wherein the cell culture medium promotes cell growth of the suspension of cells and the formation of the multicellular aggregates within the hydrogels;

exposing selected multicellular aggregates to a compound by introducing a solution comprising the compound into at least one of the supplying channel for a period of time; and assessing the viability of the multicellular aggregates exposed to the compound.

The compound may be a drug.

The multicellular aggregates may be multicellular cancer spheroids and the compound may be an anticancer drug.

The multicellular cancer spheroids may be obtained from primary cells isolated from cancer patient tissue.

The method includes a plurality of compounds being screened, and a plurality of concentrations of the compound may be screened The hydrogels containing the multicellular aggregates may be released from the microwells into the supplying channel and moved to the corresponding supplying exit for retrieval of the hydrogels from the microfluidic device.

The present disclosure provides a microfluidic device for producing multicellular aggregates in hydrogel scaffolds comprising:

at least one row having at least one microwell, each of the at least one microwell having a diameter and a height;

for each row, a supplying channel having a height, the supplying channel spanning along a length of the row and having an entry opening at one end of the supplying channel and an exit opening at the opposite end of the supplying channel, wherein each microwell is in flow connection with the corresponding supplying channel.

The at least one microwell may be a plurality of microwells.

The height of each microwell may be about larger than the diameter of each microwell. In this respect the height of each microwell may be about at least 20% larger than the diameter of the each microwell. The height of each microwell may be greater than the height of the supplying channel, and a ratio of the height of each microwell to the height of the supplying channel is at least about 4.5.

The ratio of the height of the microwells to the height of the supplying channel may be between about 4.5 to about 5.5.

The at least one microwell and corresponding supplying channel may be made PDMS.

The solution may comprise the aqueous suspension of cells comprising a plurality of different types of cells.

The solution may comprise the aqueous suspension of cells comprising a plurality of different types of cells.

The hydrogel precursor may comprise a temperature-responsive polymer. The temperature-responsive polymer may comprise CNCs having their surface functionalized with temperature-responsive polymer molecules. The CNCs may have poly(N-isopropylacrylamide) polymer chains grafted on their surface.

The CNCs may be functionalized with a copolymer of N-isopropylacrylamide and N,N'-dimethylaminoethyl methacrylate.

The present disclosure provides a microfluidic device for producing multicellular aggregates in hydrogel scaffolds comprising:

at least one row having a plurality of microwells, each microwells having a diameter and a height;

for each row, a supplying channel having an height, the supplying channel spanning along a length of the row and having an entry opening at one end of the supplying channel and an exit opening at the opposite end of the supplying channel; and wherein each microwell is in flow connection with the corresponding supplying channel and the height of microwell is about at least 20% larger than the diameter of the microwells and a ratio of the height of the microwells to the height of the supplying channel is at least about 4.5.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the drawings, in which:

FIG. 6 shows the variation in the Young's modulus of a-CNC/gelatin hydrogels with varying the concentration of gelatin.

Figure 1A:
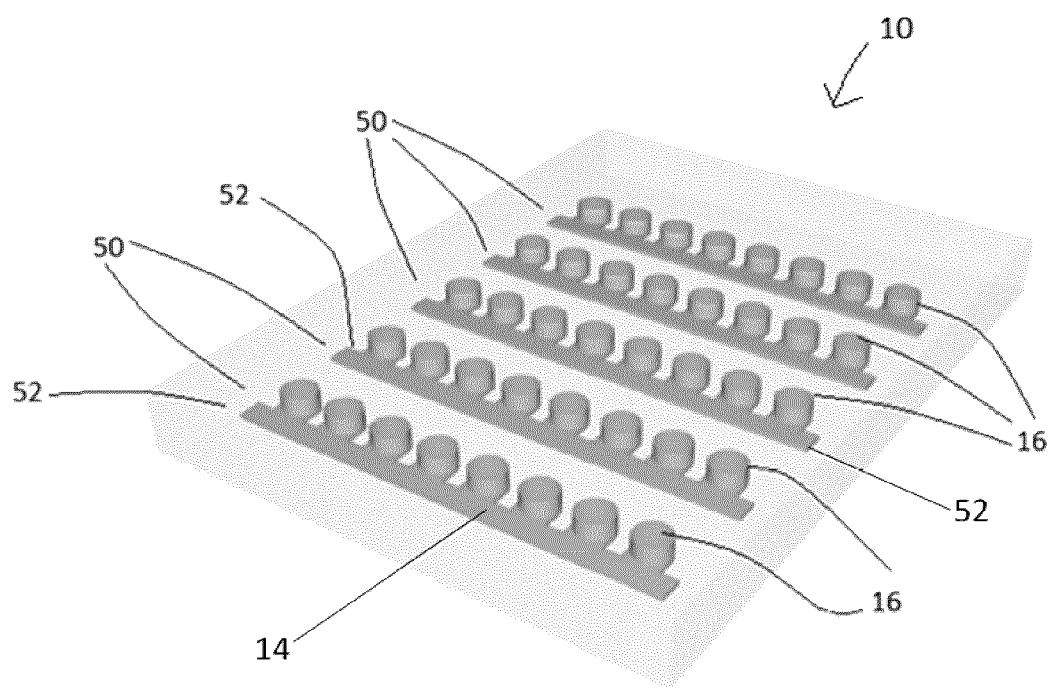
FIG. 1A is a schematic diagram of a fragment of microfluidic device showing five (5) rows of wells and channels interconnected the wells to reagent supply for the generation of 2D arrays of MCSs according to an embodiment.

bright field image of cell-laden a-CNC/gelatin hydrogels (0.75 wt. % a-CNC, and 2 wt. % gelatin); (b) fluorescence image of cell-laden a-CNC/gelatin hydrogels after 30 min of perfusing channels with 1 mg/mL solution of 70 kDa FITC-dextran at a flow rate of 1 mL/h; (c,d) fluorescence images after perfusing cell-laden hydrogels (as in b) with dye-free media at the flow rate of 1 mL/h for (c) 10 s, and (d) 100 min. Scale bars are 200 μm. Cell density is 1000 cells/4, and (e) Change in average fluorescence intensity of cell-laden hydrogels with time of washing with dye-free media.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

The present disclosure is drawn to a microfluidic (MF) device and method of formation of an array of multicellular aggregates onto the device. Multicellular cancer spheroids (MCSs) are three-dimensional cancer cell aggregates with dimensions from tens of micrometers to ~1 mm, which replicate many features of solid tumors in vivo, including extracellular matrix (ECM) deposition between the cells, strong cell-cell junctions, and gradients in nutrient concentration (Li, Y. and Kumacheva, E., Science Advances (2018) 4(4):eaas8998 entitled Hydrogel microenvironments for cancer spheroid growth and drug screening). For the purpose of this disclosure, multicellular aggregate consists of an aggregate of cells being self-organized in a three-dimensional arrangement. Furthermore, the cells within the aggregate may have formed a specific common membrane. The multicellular aggregate may be an organoid obtained with stem cells or a combination of stem cells and other cells.

Alternatively, the multicellular aggregate may be a multicellular spheroid. The multicellular spheroid may be made of cells obtained from a cancer cell line or obtained from primary cells isolated from cancer patient tissue. Such cells may be obtained from separation and isolation of individual cells from tissue biopsy. Depending on the use of the current process or device disclosed herein, the multicellular aggregate may comprise one kind of cells or a plurality of different kinds of cells resulting in heterogeneous organoids or spheroids.

According to an embodiment, the device and method may be used for screening compounds for drug discovery, for understanding mode of action of the screened compounds and for the evaluation of pharmacodynamics and/or mechanistic biomarkers. According to an embodiment, the device and method may be particularly useful in screening/studying the effect of composition, structure and properties of the environment on MCS growth OR interactions between different cells, e.g., immune cells ad cancer cells and in screening/studying the role of the composition of the cell culture media. According to an embodiment, the device and method may be particularly useful in the study and/or screening of drugs for therapeutic treatment by delivering drugs such as anticancer drugs to multicellular spheroids or organoids, both of which may be acting as microtumors when obtained from high-density cell suspensions, under dynamic conditions.

According to an embodiment, the device and method may be useful in the study of cancer spreading and/or screening of cancer drugs on multicellular spheroids or organoids, both of which may be acting as metastatis microtumors when obtained from low-density cell suspensions, under dynamic conditions.

According to an embodiment, the present invention provides means to study different stages of cancerous tumors, e.g., early stage and later stages of cancerous tumors. Cancer spheroids obtained from low-density cell suspension may be used to study/mimic tumor growths formed from individual cells. Alternatively, cancer spheroids obtained with high-density cell suspension may be used to study/mimic later stage of tumor growth once the cells have organized themselves into a cancerous tumor.

According to an embodiment, the anticancer drugs may target various types of cancer. For example, the anticancer drugs may target breast cancer. Alternatively, the anticancer drugs may target pancreatic cancer.

One advantage of the present invention is the use of multicellular spheroids obtained from primary cells isolated from cancer patient tissue rendering possible a personalized screening of compounds. According to an embodiment, the device and method may provide the formation of a large arrays of uniformly-sized multicellular aggregates of various sizes under continuous close-to-physiological flow conditions in microfluidic devices. The multicellular aggregates may grow to become uniformly-sized multicellular cancer spheroids or organoids. According to an embodiment, the device and method may be useful in screening compounds by the delivery of such compounds to the multicellular aggregates under dynamic conditions.

According to an embodiment, the device and method disclosed herein may provide the formation of a large arrays of uniformly-sized multicellular aggregates, such as spheroids or organoids, which may be released from the device for retrieval of the spheroids or organoids from the microfluidic device. These spheroids or organoids may be released using different means known to the skilled person in the art (Li, Y. et al., Angew Chem Int Ed Engl (2017)56(22):6083-6087 entitled Supramolecular Nanofibrillar Thermoreversible Hydrogel for Growth and Release of Cancer Spheroids; Li, Y. and Kumacheva, E., Science Advances (2018) 4(4): eaas8998 entitled Hydrogel microenvironments for cancer spheroid growth and drug screening; and Thérien-Aubin, H., et al., Biomacromolecules (2016) 17(10):3244-3251 entitled Temperature-Responsive Nanofibrillar Hydrogels for Cell Encapsulation). They may be released by enzymatic or chemical-mediated hydrogel digestion/lysis, using mechanical hydrogel disruption, hydrogel photodegradation. Alternatively, the spheroids or organoids may be "washed away" by strongly increasing the flow rate in the microfluidic device. According to another embodiment, the spheroids or organoids may be released by inducing liquefaction of a temperature-responsive hydrogel at a reduced physiologically acceptable temperature.

According to an embodiment, as shown in FIG. 1A, a microfluidic device 10 has a plurality of parallel rows 50. Each row 50 comprises a plurality of cylindrical microwells 16 in which a large arrays of multicellular aggregates may be grown in tissue-mimicking hydrogel scaffolds under close-to-physiological flow conditions in the microwells 16. For each row 50, a supplying channel 14 spans along the length of the row 50 and is in flow communication with the respective microwells 16. The supplying channel 14 has an exposed opening at both of its ends 52 acting either as an entry opening or an exit opening for the circulation within a given row 50 of fluids such as wetting agents, solutions comprising aqueous suspensions of cells and an hydrogel precursor, and the cell culture medium for the supply of the nutrition medium and/or compound to be screened.

Figure 1B:
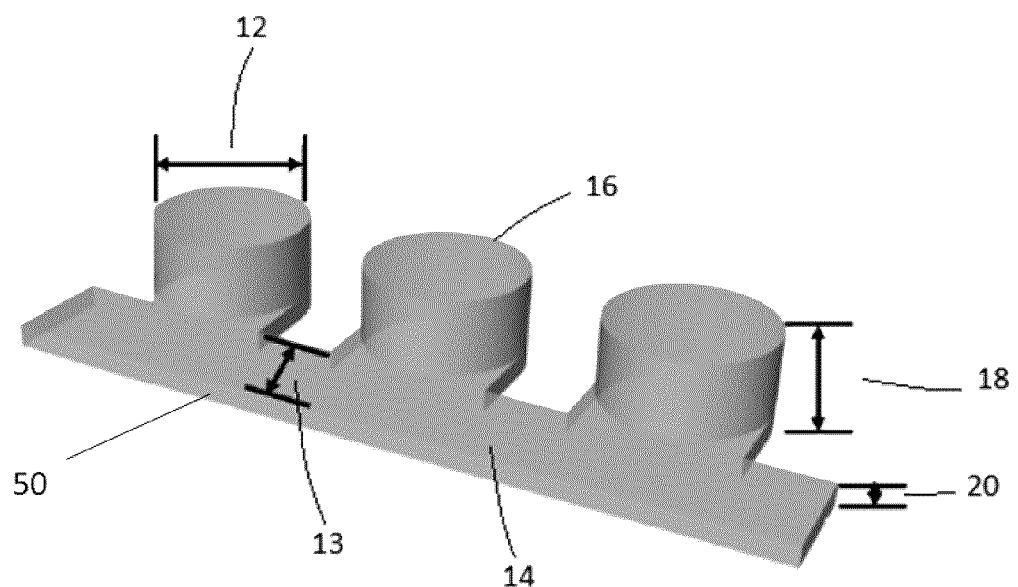
FIG. 1B is an expanded view of the microfluidic device of FIG. 1A showing several wells in one of the rows connected fluid communication with the corresponding channel.
Figure 1C:
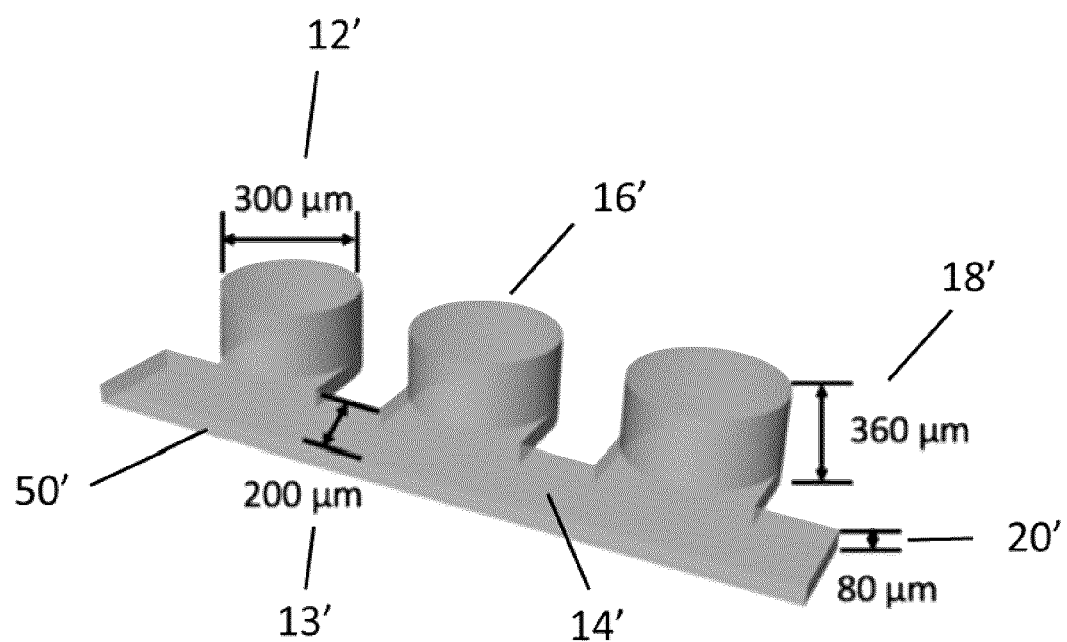
FIG. 1C is an expanded view of a microfluidic device showing several wells in one of the rows connected fluid communication with the corresponding channel and their respective dimensions according to an embodiment.

FIG. 1B shows an expanded view of three microwells 16 in one of the rows 50 from FIG. 1A along with the section of the supplying channel 14 that provides flow communication between the microwells 16 and the various reagent sources (not shown). As shown in FIG. 1B, the microwells 16 have a diameter 12 and a height 18 and the supplying channel 14 has a width 13 and a height 20.

In an embodiment, the microwells 16 of the microfluidic device 10 may have a diameter 12 between the range of about 100 to about 1000 μm and a height 18 of about between the range of about 120 to about 1200 μm.

According to an embodiment the height 18 of the microwells is larger than the diameter 12 of the microwells 16. Alternatively, the height 18 of the microwells 16 may be at least 20% larger than the diameter 12 to avoid the overgrowth of the multicellular aggregates and the swelling of the hydrogels into the supplying channel 14. Alternatively the height 18 of the microwells may be about 20% larger than the diameter 12. Since the dimensions of the device 10 may be tailored to the preferences of the user, as long as the ratio diameter/height for each microwell 16 is maintained, the diameter 12 of the microwells 16 may be varied over the microwells array in such ways that the resulting multicellular aggregates may have a distribution of diameters. Obtaining multicellular aggregates with a diversity of diameters allows the user to explore the drug efficiency for multicellular aggregates with varying dimensions.

According to an embodiment, to achieve the formation of the cell-laden precursor droplets and prevent overgrowth of the multicellular aggregates and the swelling of the hydrogels in the supplying channel 14, the height 18 of the microwells 16 is larger than the height 20 of the supplying channel 14. Alternatively, the ratio of the height 18 of the microwells 16 to the height 20 of the supplying channel 14 is at least about 4.5. The ratio is dependent on the material used for the fabrication of the microfluidic device and the wetting agent used in the method and system of the present invention. Alternatively, the ratio of the height 18 of the microwells 16 to the height 20 of the supplying channel 14 is between about 4.5 to about 5.5. This ratio was found to be good when the microfluidic device was made with polydimethylsiloxane (PDMS) and the used wetting agent comprised a fluorinated oil such as block copolymer perfluorinated polyether-b-(polypropylene glycol-polyethylene glycol-polypropylene glycol)-b-perfluorinated polyether. However, it will be appreciated that this ratio may change when different fabrication material and wetting agent combinations are used. In a preferred embodiment, the height 18 of microwells 16 is about 20% larger than the diameter 12 of the microwells 16 and the ratio of the height 18 of the microwells 16 to the height 20 of the supplying channel 14 is between about 4.5 to about 5.5. Furthermore, the excess swelling may be minimized by adjusting the concentration of hydrogel precursor in the aqueous solution.

Maintaining this ratio between dimensions 18 and 20 enables the formation of a relief volume between the top of the cell-laden droplet and the top of the microwell 16 that the droplet is contained in. This relief volume functions to limit the risk of hydrogel over-swelling or over-growth in multicellular aggregates by providing an extra volume for hydrogel swelling and growth of the cells to occur in the z-direction of the microwell 16. The spillage of the cells into the supplying channel 14 is undesirable as it may lead to flow-driven loss of the cells from the multicellular spheroids.

Fabrication of the Microfluidic Devices

Figure 3:
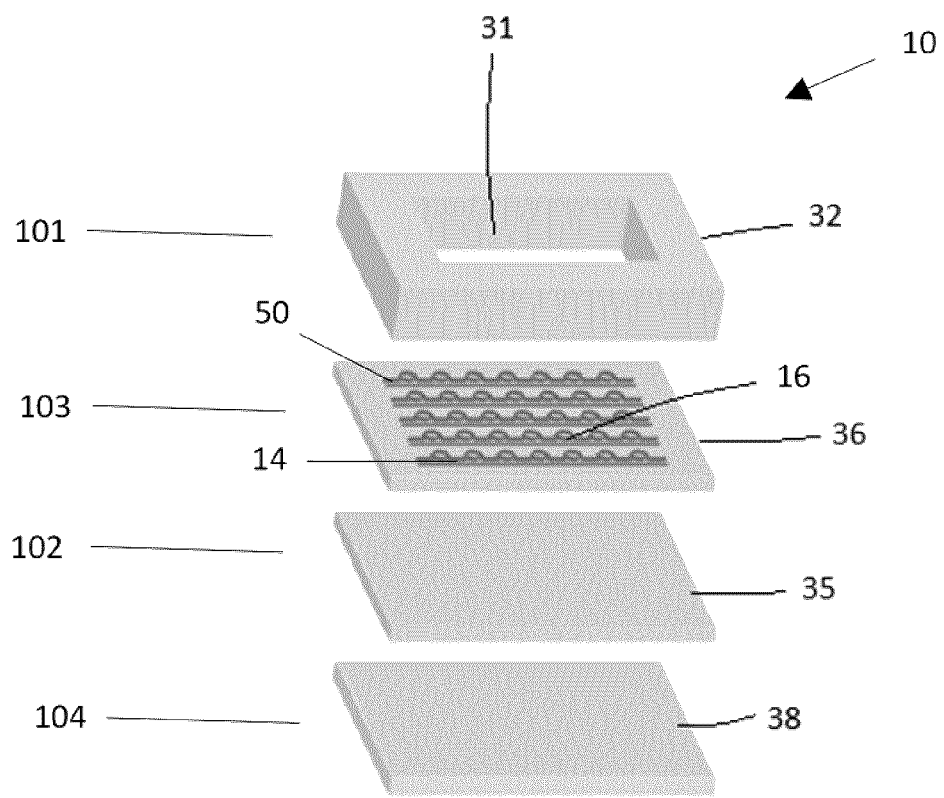
FIG. 3 shows an exploded perspective view of an assembly of multiple layers of a microfluidic device according to an embodiment.

According to one embodiment, as shown in FIG. 3, the microfluidic device 10 may comprise four different layers. These layers include a first layer 101 comprising a rectangular silicone base 3 with a mounted glass slide 31 and a second layer 102 that is a silicone-based sheet 35 with a similar thickness to the first layer. The third layer 103 is likewise composed of silicone and contains an array 36 of microwells 16, the array 36 is composed of one or more rows 50, each row 50 having a plurality of microwells 16. Each of the microwells 16 in the various rows 50 is in individual flow connection to a supplying channel 14 which spans the length of the row 50 and contains an exposed opening both of its ends of the supplying channel 14. Lastly, a fourth layer 104 has a base 38 layer which is also composed of silicon and is attached to the bottom side of the device 10. It is necessary for the MF-MSF platform to be robust, simple to fabricate and have a relatively low unit cost. It will be appreciated by those skilled in the art that polymeric materials other than silicone-based polymers may be used.

According to an embodiment, the four-layer device disclose herein may be partially fabricated in polydimethylsiloxane (PDMS) using soft lithography technique known in the art. Such technique may be found at http://www.elveflow.com/microfluidic-tutorials/soft-lithography-reviews-and-tutorials/introduction-in-soft-lithography/introduction-about-soft-lithography-and-polymer-molding-for-microfluidic/. Soft lithography encompasses a collection of fabrication methods that are based on the use of a patterned layer of exposed PDMS. In one possible embodiment, the device's four silicon layers as disclosed above may be formed through the use of the soft-lithography deposition. According to an embodiment, the device 10 may include at least one row or a plurality of parallel rows, with each row having at least one well. According to an embodiment, the device 10 may include anywhere from 1 to 40 parallel rows 50, each row 50 may contain from 1 to 300 wells or alternatively from 50 to 300 wells, depending on the size of microwells 16.

According to an embodiment, the device 10 may have overall dimensions of 75×50 mm. When having such dimensions, the device 10 may have 2000-12000 microwells depending on the microwell diameters 12. The dimensions first layer 101 and second layer 102 are approximately 75×50×1 mm. These two layers are bonded together after fabrication. The third layer 103 having dimensions of 75×50×0.5 mm was bonded to the second layer 102 with the features of the supplying channels 14 and microwells 16 facing the second layer 102. Finally, the fourth layer 104 is fabricated containing a reservoir filled with HBSS or additional saline solution to prevent evaporation of water from the multicellular aggregates and is then bonded to the third layer 103. The device 10 is then heated in an oven for 12 hr at 115° C. to activate the hydrophobicity of the layers.

During the microfabrication of the microfluidic device layers, the silicon masters when prepared by 3D printing may adhere to PDMS molds, resulting in the distortion of the microwell shape and size. As both the size and shape of the microwells 16 are critical to the controlled formation of the multicellular aggregate, the fabrication method may include steps to address this issue. Specifically, in one non limiting example, the surface of the 3D printed masters may be treated with trichloro (1H,1H,2H,2H-perfluorooctyl) silane vapor. The treatment substrate for the 3D printed masters may be a variety of fluorinated/chlorinated aliphatic silanes which are suitable for achieving adequate fluid film lubrication. The surface of the masters is then, in this particular embodiment, controllably etched with $H_2SO_4$. The etching is needed in order to compensate for resolution limitations in the 3D printer which may result in the surface of microwells 16 being intrinsically rough.

In a non-limiting embodiment, the fabrication method of the microfluidic device layers and assembly into device 10 may utilize photolithography to fabricate microfluidic devices for MF-MCS platform, micromachining, etching or laser ablation In another embodiment, the fabrication method of the microfluidic device layers and assembly into device 10 may utilize 3D printing technologies. The utilization of 3D printing may make microfluidic devices more cost-efficient and versatile. Furthermore, the fabrication of the microfluidic device through 3D printing technology may enable growth of multicellular aggregates such as multicellular spheroids with dimensions larger than 500 μm and the growth of various sized multicellular spheroids in the same device, thus enabling drug screening for microtumors with different dimensions.

Method For Producing Multicellular Aggregates

According to an embodiment, a method for producing of an array of multicellular aggregates onto the microfluidic device is provided. As previously mentioned, the multicellular aggregates consist of aggregates of cells being self-organized in a three-dimensional arrangement. The multicellular aggregates may be organoids obtained with stem cells or a combination of stem cells and other cells.

Alternatively, the multicellular aggregates may be multicellular spheroids. The multicellular spheroids may be made of cells obtained from a cancer cell line or cells obtained from primary cells isolated from cancer patient tissue. Such cells may be obtained from separation and isolation from tissue biopsy. Depending on the use of the current invention, the multicellular aggregates may comprise one kind of cells or a plurality of different kinds of cells resulting in heterogeneous organoids or spheroids.

According to an embodiment, the multicellular aggregates such as multicellular spheroids or organoids may be obtained from high-density cell suspensions or low-density cell suspensions.

According to an embodiment, multicellular aggregate such as multicellular spheroids or organoids may be obtained with varying dimensions in the hydrogels having different properties/characteristics in separate rows of the microfluidic device 10.

According to an embodiment, multicellular aggregates such as organoids, multicellular spheroids or spheroids may be formed in a multi-step procedure, which includes the generation of uniformly-sized droplets from a dense suspension of cells in a solution of the hydrogel precursor in the microwells 16 of microfluidic device 10 and chemically or physically crosslinking of the hydrogel precursor, thus transforming droplets into cell-laden micrometer-size hydrogels and MCS formation and growth.

Figure 2A:
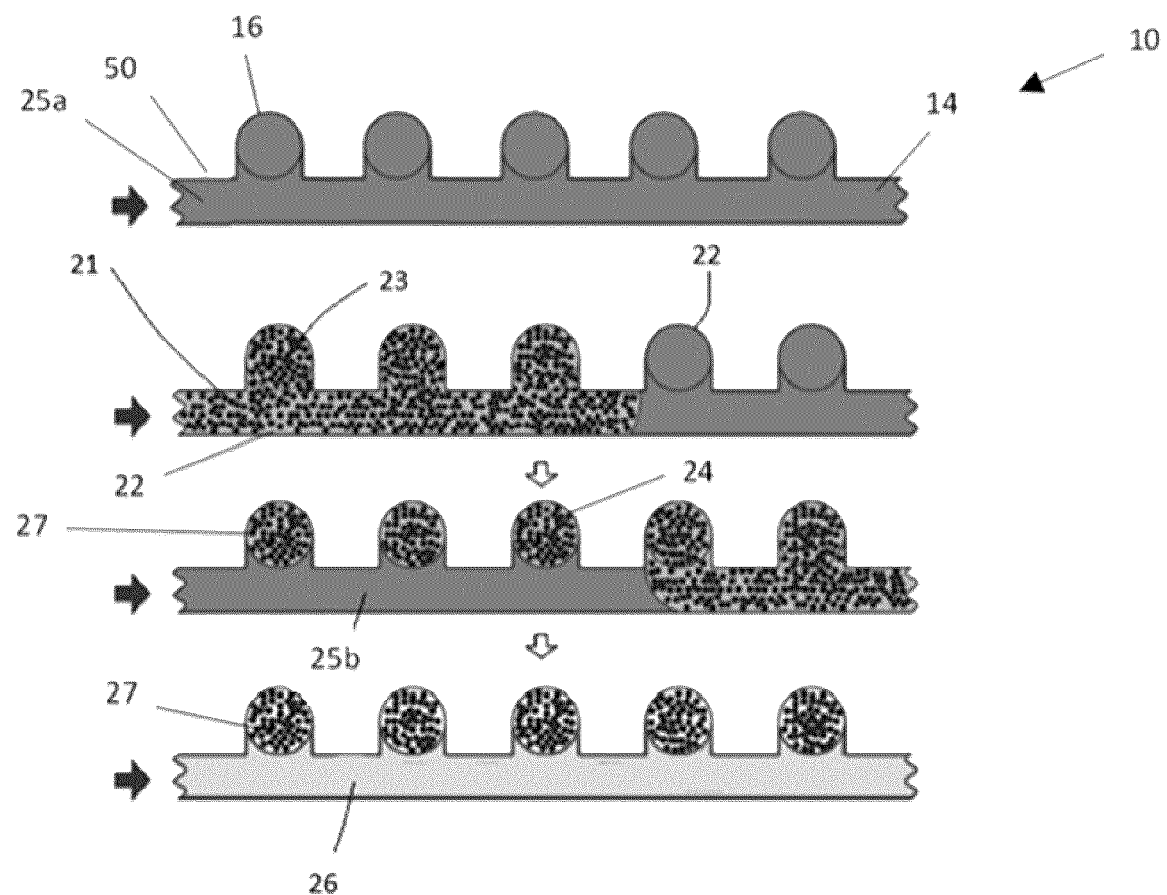
FIG. 2A is schematic side view of MF generation of ECM-MCSs using high-density cell suspension showing from the upper panel to the lower panel different stages in the process of producing the MCSs according to an embodiment.

According to an embodiment, as shown in FIG. 2A, a method of rapidly producing uniformly-sized multicellular aggregates from a high-density cell suspension using the microfluidic device 10 of the present invention. The method may comprise the steps of:

1) introducing a first wetting agent 25a into the supplying channel 14 and corresponding microwells 16 of at least one row 50 of the microfluidic device 10;

2) introducing a solution 21 comprising an aqueous high-density suspension of cells 23 and an hydrogel precursor 22 into the supplying channel 14 and corresponding microwells 16 of the at least one row 50 of the microfluidic device 10 to displace the first wetting agent 25a within the supplying channel 14 and the microwells 16 with the solution 21;

3) introducing a second wetting agent 25b into the supplying channel 14 of the at least one row 50 of the microfluidic device 10 to displace the solution 21 within the supplying channel 14 with the second wetting agent 25b, wherein displacing the solution 21 in the supplying channel 14 with the second wetting agent 25b induces the formation of droplets 24 containing the aqueous high-density suspension of cells 23 and the hydrogel precursor 22 within the microwells 16 of the at least one row 50 of the microfluidic device 10. The formation of the droplets 24 containing the aqueous suspension of cells 23 and the hydrogel precursor 22 is caused by reduction of interfacial area or in surface energy when the aqueous suspension contacts with the wetting agent 25b;

4) inducing the gelation of the hydrogel precursor 22 within the droplets 24 to form a hydrogel 27 seeded with the high-density suspension of cells 23 within the microwells 16; and 5) introducing a first cell culture medium 26 into the supplying channel 14 of the at least one row 50 of the microfluidic device 10 to displace the second wetting agent 25b in the supplying channel 14.

According to an embodiment, the solution 21 comprising the aqueous high-density suspension of cells and the hydrogel precursor 22 may have a cell concentration ranging from $1\times10^7$ to $10\times10^7$ cells/mL. For examples, the solution 21 may have a cell concentration of $3\times10^7$ cells/mL to obtain high-density spheroids.

Figure 2B:
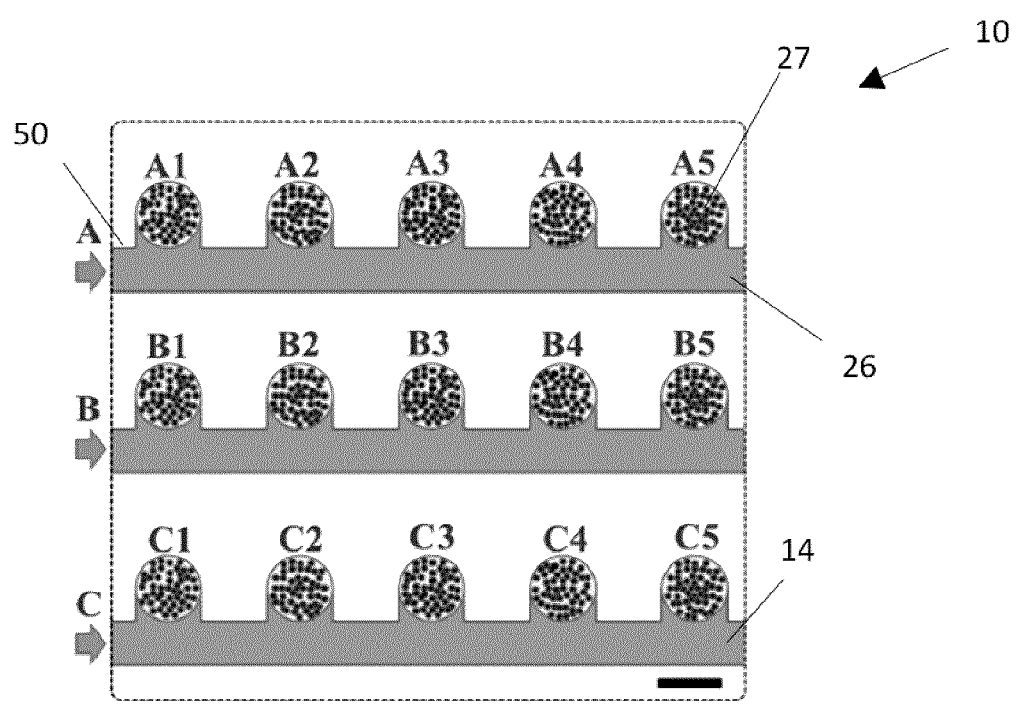
FIG. 2B is a schematic side view of the 2D arrays of indexed ECM-MCSs.

According an embodiment, as shown in FIG. 2B, the method may further comprise the step of continuously flowing a second cell culture medium 26 into the supplying channel 14 of the at least one row 50 of the microfluidic device 10 for the during of the studies on the products in microwells 16, wherein the cell culture medium 26 promotes cell growth of the suspension of cells 23 and the formation of the multicellular aggregates 28 within the hydrogels 27. According to an embodiment, when the cell culture medium 26 may be continuously flowing into the support channel 14 of the at least one row 50 of the microfluidic device 10, the continuous flow may be maintained to promote the formation of multicellular aggregates such as multicellular spheroids or organoids within about 1 to about 3 days.

According to an embodiment, the first and second cell culture media are similar. Alternatively, they may be distinct.

Figure 2C:
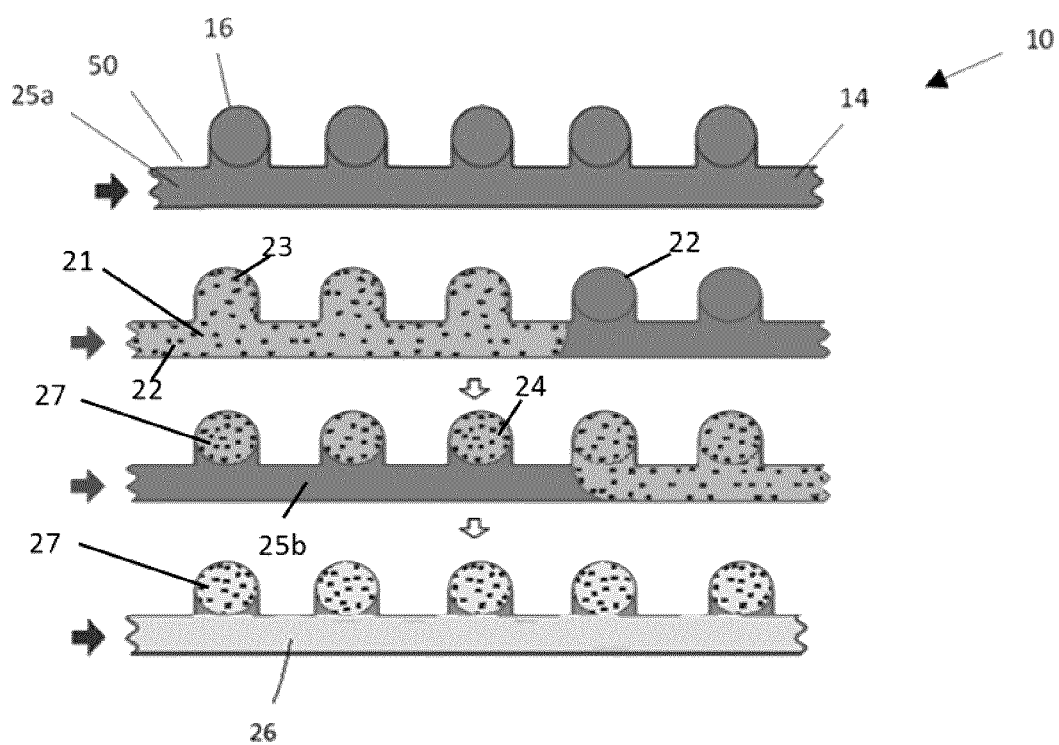
FIG. 2C is schematic side view of MF generation of ECM-MCSs using low-density cell suspension showing from the upper panel to the lower panel different stages in the process of producing the MCSs according to an embodiment.

According to another embodiment, multicellular aggregates may be formed using a multi-step procedure as described above but using a low-density cell suspension as shown in FIG. 2C.

The method may comprise the steps of:

1) introducing a first wetting agent 25a into the supplying channel 14 and corresponding microwells 16 of at least one row 50 of the microfluidic device 10;

2) introducing a solution 21 comprising an aqueous low-density suspension of cells 23' and a hydrogel precursor 22 into the supplying channel 14 and corresponding microwells 16 of the at least one row 50 of the microfluidic device 10 to displace the first wetting agent 25a within the supplying channel 14 and the microwells 16 with the solution 21;

3) introducing a second wetting agent 25b into the supplying channel 14 of the at least one row 50 of the microfluidic device 10 to displace the solution 21 within the supplying channel 14 with the second wetting agent 25b, wherein displacing the solution 21 in the supplying channel 14 with the second wetting agent 25b induces the formation of droplets 24 containing the aqueous low-density suspension of cells 23' and the hydrogel precursor 22 within the microwells 16 of the at least one row 50 of the microfluidic device 10. The formation of the droplets 24 containing the aqueous suspension of cells 23 and the hydrogel precursor 22 is caused by reduction of interfacial area or in surface energy when the aqueous suspension contacts with the wetting agent 25b;

4) inducing the gelation of the hydrogel precursor 22 within the droplets 24 to form a hydrogel 27 seeded with the low-density suspension of cells 23' within the microwells 16; and 5) introducing a first cell culture medium 26 into the supplying channel 14 of the at least one row 50 of the microfluidic device 10 to displace the second wetting agent 25b in the supplying channel 14.

According to an embodiment, the solution 21 comprising the aqueous low-density suspension of cells and the hydrogel precursor 22 may have a cell concentration ranging from 100 to 1000 cells/μl. For examples, the solution 21 may have a cell concentration of 1000 cells/μL to obtain low-density spheroids.

According to an embodiment, the multicellular aggregates such as multicellular spheroids and organoids may be obtained with the use of a solution comprising the aqueous suspension of cells having a plurality of different types of cells.

According to an embodiment, the multicellular aggregates such as multicellular spheroids or organoids may have diverse range of diameters suitable for a given application or use. Non-limiting diameters may range from at least 40 μm, and some are suitable in a range from about 40 to about 1000 μm or from about 50 to about 1000 μm, or higher than 1000 μm. Alternatively, the multicellular aggregates may have a diameter ranging from about 50 to 300 μm.

According to an embodiment, the method may further comprise the step of releasing the multicellular aggregates 26 from the microwells 16 into the supplying channel 14 and moving the aggregates to the corresponding supplying exit for retrieval of the hydrogels 27 from the microfluidic device 10. The multicellular aggregates 26 such as spheroids or organoids may be released using different means known to the skilled person in the art. They may be released by enzymatic or chemical-mediated hydrogel digestion/lysis, using mechanical hydrogel disruption, hydrogel photodegradation. Alternatively, the spheroids or organoids may be "washed away" by strongly increasing the flow rate in the microfluidic device. According to another embodiment, the spheroids or organoids may be released by inducing liquefaction of a temperature-responsive hydrogel at a reduced physiologically acceptable temperature.

According to an embodiment, the first agent 25a and second wetting agents 25b may be the same. The wetting agents 25a and 25b are a liquid that is immiscible in water. For example, the wetting agents 25a and 25b may be an organic liquid such as oil.

According to an embodiment, the wetting agent 25a and 25b comprise a fluorinated oil. According to another embodiment, the wetting agent 25a and 25b comprise a fluorinated oil and a surfactant. The surfactant may be, but is not limited to a block copolymer perfluorinated polyether-b-(polypropylene glycol-polyethylene glycol-polypropylene glycol)-b-perfluorinated polyether. Non-limiting examples of wetting agent are fluorinated oil is mixed with 0.1 wt %, 0.5 wt. % or 1 wt % block copolymer perfluorinated polyether-b-(polypropylene glycol-polyethylene glycol-polypropylene glycol)-b-perfluorinated polyether.

Because the aqueous solution 21 may wet the surface of microwells 16 and supplying channel 14 during the formation of cell-laden precursor droplets 24 and therefore interfere with the generation of uniformly-sized droplets 24 and by extent of this, with the formation of accurately sized multicellular spheroids or organoids 26 within the hydrogels 27, wetting agent 25a is used to wet the walls of the microwells 16 and supplying channel 14. When the aqueous solution 21 comprising cells 23 and a hydrogel precursor 22 enters the supplying channel 14 and microwells 16, the aqueous phase consisting of the aqueous solution 21 is surrounded by the oil 25 in the microwells 16 adopts a more spherical shape than in the supplying channel 14 due to its reduced interfacial area.

A role of the wetting agent 25b is to form droplets in the wells 16, which will form microgels upon gelation, and to wash the solution 21 from the supplying channel 14 while the solution 21 is contained within the microwells 16 as captured as droplets 24. When introducing the wetting agent 25b into the supplying channel 14, the mixture of precursor/cell becomes primed into droplets 24 and retained into the microwells 16 as the droplets 24 would have to deform in order to exit the microwells 16.

According to an embodiment, the first step of introducing a first wetting agent 25a into the supplying channel 14 and corresponding microwells 16 may comprise the sub-step of first filling the supplying channel 14 and microwells 16 with a fluorinated oil and then replacing the fluorinated oil with a solution of fluorinated oil and surfactant such as a solution of fluorinated oil and 0.5 wt. % block copolymer perfluorinated polyether-b-(polypropylene glycol-polyethylene glycolpolypropyleneglycol)-b-perfluorinated polyether (PFPE-b-(PPG-PEG-PPG)-b-PFPE).

Hydrogels Laden With Cells For The Growth Of Uniformly-Sized Multicellular Aggregates Such As Multicellular Spheroids And Organoids To achieve adequate functionality for a variety of screening applications, the multicellular spheroids or organoids may form in a variety of environments having different stiffness and permeability properties. The stiffness and permeability of the hydrogel scaffolds will mimic the characteristics of the environments in which the studies cells are usually found. As such, a skilled person would understand the need to select appropriate hydrogel precursors and the need to tune the formulation of solution of hydrogel precursors to obtain a hydrogel scaffold with suitable characteristics while mimicking the environment from which the cells forming the multicellular spheroids or organoids growth are derived.

According to an embodiment, the hydrogel scaffold may be obtained with the use of a hydrogel precursor of synthetic monomers or polymers, biopolymers or combination of polymers and/or biopolymers. Non-limiting examples of polymers or biopolymers for the formation of hydrogels are collagen, gelatin, fibrin, agarose, alginate, polyacrylamide, polyethylene glycol, hyaluronic acid, cellulose derivatives, polypeptides, and mixtures of these polymers and nanoparticles functionalized with biopolymers or synthetic polymers.

According to an embodiment, the hydrogel scaffold may be obtained via either chemical crosslinking, physical crosslinking or combination of chemical and physical crosslinking of the precursor as long as the hydrogel scaffold remains intact when subjected to continuous flows within the microfluidic device.

According to an embodiment, the flow within the microfluidic device may be set to flow rates up to 20 mL/hour without damaging the microfluidic device. According to another embodiment, flow rates between the range of 0.1 to 0.01 mL/hour may be used for cell culture and droplet generation.

The skilled person would know that any hydrogel precursor may be used as long as 1) the precursor and resulting hydrogel scaffold is non-toxic and biocompatible to the cells, 2) the desired gelation time, stiffness, permeability/diffusion, bioadhesion are obtained and 3) the resulting hydrogel scaffold would be stable and withstand the shear forces when subjected to the continuous flows within the microfluidic device. The skilled person will also understand that the amount of precursor and degree of crosslinking may be varied to obtain hydrogel scaffolds with the desired characteristics, e.g., gelation time, stiffness, permeability/diffusion, as long as the cells may survive in the hydrogel scaffolds and formed multicellular spheroids or organoids.

According to an embodiment, the hydrogel precursor may be functionalized with growth factors and/or peptides fragments to promote cell growth, survival and transformation into a spheroid or organoid.

According to an embodiment, prior using the method for producing multicellular aggregates of the present disclosure, the skilled person may have use cell suspension in macroscopic gels as a first screening to identify which hydrogel precursor formulation would result in a hydrogel with suitable characteristics such as stiffness and permeability/diffusion. Once the screening has been done and the properties of the hydrogel scaffold have been tuned, the multicellular aggregates may be prepared using the microfluidic device.

According to an embodiment, depending on the selected precursor, the degree of crosslinking of the hydrogel scaffold and the total amount of precursor in the solution may be varied to enable the tuning of the stiffness of the hydrogel scaffold from tens of Pa to tens of kPa to provide the cells with an environment with suitable stiffness. According to an embodiment, the hydrogel scaffold may have a stiffness ranging between about 10 Pa to hundreds kPa or about 50 Pa about 100Kpa. According to another embodiment, the hydrogel scaffold may have a stiffness ranging between about 10 Pa to about 20 kPa. The skilled person would understand that the mechanical properties of the hydrogel scaffolds should be tailored to the mechanical properties of the environments the hydrogel scaffolds are mimicking.

For example, for soft tissues and organs, the stiffness may range from 0.1 kPa to 1Mpa. The stiffness for brain tissues may range from 0.1 kPa to 1 kPa, the stiffness for skin, spleen or pancreas tissues may range from 1 kPa to 10 kPA, the stiffness for gland and muscle tissues may range from 8 kPa to 17 kPa, the stiffness for tendon tissues may range from 30 kPa to 50 kPa, the stiffness for cartilage tissues may range from 220 kPa to 550 kPa, the stiffness for bone tissues may range from 10 MPA to 15 MPa and the stiffness for breast tissues may range from 7 kPA to 30 kPA (Liu, J. et al., Int. J. Mol. Sci. (2015) 16: 15997-16016 entitled Hydrogels for engineering of perfusable vascular networks; Chen, H. et al., ACS Appl. Mater. Interfaces (2017)9: 21059-21064 (2017) entitled Microfluidic Generation of High-Viscosity Droplets by Surface-Controlled Breakup of Segment Flow; Leipzig, N. D. and Shoichet, M. S., Biomaterials (2009) 30: 6867-6878 entitled The Effect of Substrate Stiffness on Adult Neural Stem Cell Behavior; Levental, I. et al., Soft Matter (2007) 3: 299-306 entitled A. Soft Biological Materials and Their Impact on Cell Function; and Lorenzen, J. et al, Rofo (2002) 174(7):830-4 entitled MR elastography of the breast:preliminary clinical results) The skilled person will understand that these ranges may vary depending on the publication source and also the method use to characterize the stiffness of the tissues.

Similarly, depending on the selected precursor, the gelation time, which is needed for the generation of precursor droplets and their gelation in the microwells 16 of the microfluidic device 10, may be tuned by varying the degree of crosslinking of the hydrogel scaffold and the concentration of the hydrogel precursor. The gelation time may range between the order of about 10 minutes to hours depending on the nature of the hydrogel precursor, the concentration of the hydrogel precursor, the type of crosslinking and the degree of crosslinking of the hydrogel scaffold and the method of gelation being employed. For example, the time of gelation may range from about 30 minutes to about 1.5 hours and more preferably from about 1 to about 1.5 hours for enabling the generation of cell-laden droplets and support cell viability. Although longer gelation time may be possible, it will be appreciated that gelation times which are too long may be problematic and/or not suitable due to cell death.

According to an embodiment, depending on the selected precursor, the degree of crosslinking of the hydrogel scaffold and the total amount of precursor in the solution may be varied to enable the tuning of the permeability of the hydrogel scaffold. Proper permeability allows the transport of nutrients, chemicals or drugs from the media to the multicellular aggregates, e.g., spheroids or organoids. Furthermore, proper permeability promotes cell survival, cell growth, transformation into multicellular spheroids or organoids, survival of the multicellular spheroids or organoids and diffusion of the screened compounds to the multicellular spheroids or organoids. The permeability of the hydrogel scaffolds, depending on the selected precursor, the degree of crosslinking of the hydrogel scaffold and the total amount of precursor in the solution, may be at least $10^{-13}$ $cm^2$. For example, the permeability may be between about $10^{-13}$ to about $10^{-9}$ $cm^2$.

Chemically-Crosslinked Hydrogel Scaffolds

According to an embodiment, any chemically-crosslinked hydrogel scaffolds obtained via the covalent bonding between polymer chains may be used as long as the hydrogel scaffolds have suitable characteristics and allow the formation and survival of multicellular aggregates or spheroids. The crosslink formation may be carried out by the addition of small cross-linkers molecules, polymer-polymer conjugation, photosensitive agents or by enzyme catalyzed reaction According to another embodiment, a chemically cross-linked hydrogel scaffold may be derived from flexible biopolymers or polymers containing free amine groups and aldehyde-modified cellulose nanocrystals (a-CNCs). Because CNCs are rod-like, rigid nanoparticles with an average length and diameter of 100-300 nm and 5-20 nm, respectively, which assemble into a nanofibrillar network, the resulting a-CNC-derived hydrogel scaffolds may have a scaffolding structure that resembles the structure of the ECM proteins. CNCs may be surface-modified by oxidative cleavage at the C2-C3 bond in the presence of periodate, which yields dialdehyde groups at the respective carbon atoms. The aldehydes present on the a-CNCs react with the free amine groups present on the flexible biopolymers or polymers to form imine crosslinks resulting in a hydrogel scaffold that may be used in the synthesis of the hydrogel-based multicellular spheroids.

Figure 4:
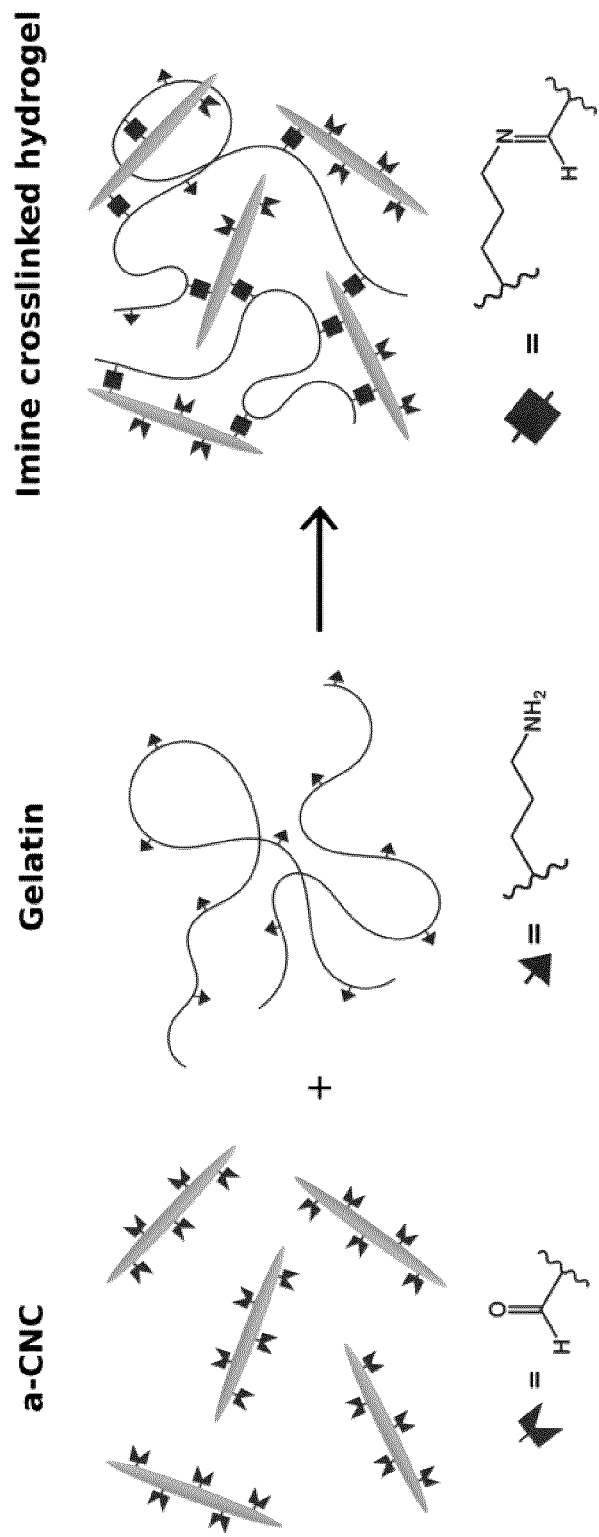
FIG. 4 shows a schematic of the formation of a-CNC/gelatin hydrogels.

According to another embodiment, the chemically cross-linked hydrogel scaffold is obtained from the crosslinking of free amine groups present on gelatin and the aldehyde groups present on the a-CNCs as shown in FIG. 4. Gelatin which is denaturated collagen. It contains Arg-Gly-Asp (RGD) sequences which are available to bind to integrin receptors on the cell surfaces, thereby advantageously making the hydrogel scaffold bioadhesive. The rationale behind the use of a-CNCs/gelatin hydrogels is that the a-CNCs may act as a filamentous building block (responsible for the nanofibrillar structure), while the gelatin may act bioadhesive soft component resulting in a hydrogel mimicking the ECM environment which may be used in the synthesis of the hydrogel-based multicellular spheroids.

An additional advantage of using a-CNCs/gelatin hydrogel is that both constituents are nontoxic and cytocompatible to a variety of cell types both in culture media and in hydrogel constructs.

Multicellular Spheroids in a-CNCs/Gelatin Hydrogels
Materials:

Type A gelatin (300 g bloom), sodium periodate, butyl acrylate, 9-vinyl anthracene, potassium persulfate, sodium dodecyl sulfate, and acetic acid were purchased from Sigma-Aldrich, Canada and used without further purification, unless otherwise specified. An aqueous 12.2 wt % suspension of CNCs was purchased from the University of Maine Process Development Center and dialyzed for 7 days against Milli-Q grade distilled deionized water (DI, 18.2 MΩ cm resistivity) before use.

Surface Modification of CNCs with Aldehyde Groups:

Aldehyde-functionalized CNCs were prepared according to the protocol described by Prince at al. (Prince, E., et al, Biomacromolecules (2018) 19,1276-1284 entitled Patterning of Structurally Anisotropic Composite Hydrogel Sheets, which is incorporated herein by reference. Briefly, the oxidation of the surface hydroxyl groups on CNCs to yield a-CNCs was performed by adding sodium periodate (NaIO4) to a 1 wt % suspension of CNCs at a NaIO4/CNC weight ratio of 4:1. The pH was adjusted to 3.5 with acetic acid. The flask was covered with aluminum foil to prevent photodecomposition of NaIO4. The suspension was stirred at 25° C. for 2 h and subsequently quenched by adding ethylene glycol. The suspension of a-CNCs was dialyzed against deionized water for 7 days, with replacement twice a day, and then concentrated by rotary evaporation.

The presence of aldehyde groups on the CNC surface was confirmed with attenuated total reflectance Fourier transform infrared spectroscopy (ATR-FTIR) using a Bruker Vertex 70 spectrometer with a 1.85 mm diameter diamond crystal. The aldehyde group content of the CNC surface was determined by first converting the aldehydes to carboxylic acid groups in 0.1 M NaOH via the intramolecular Cannizzaro reaction and subsequently titrating with sulfuric acid to determine the consumption of hydroxide ions.

Quantification of Amine Groups on Gelatin:

The TNBS (trinitrobenzenesulfonic acid) assay was used to quantify the number of primary amine groups in gelatin, as described by Prince et al. Briefly, gelatin was dissolved in 0.1 M sodium carbonate buffer (pH=9) to a final concentration of 0.5 wt %. Trinitrobenzenesulfonic acid (TNBS) was added to the solution to a final concentration of 0.1 w/v %, and the solution was equilibrated for 4 h at 37° C. The absorbance of the solution was measured at $\lambda$=500 nm. A calibration curve was prepared by measuring the absorbance of the solution at $\lambda$=500 nm for standard solutions of beta alanine in 0.1 M sodium carbonate buffer, containing 0.1 w/v % TNBS.

Characterization of the Molar Ratio between Aldehyde Groups on a-CNCs and Amine Groups in Gelatin:

The molar ratio between the amine groups on gelatin and aldehyde groups on a-CNCs determines the number of complimentary cross-linkable groups. The molar ratio was determined by the following assay, as described by Prince et al. The concentration of aldehyde groups in the a-CNCs was characterized by first converting these groups to carboxylic acid groups in 0.1M NaOH using an intra-molecular Cannizzaro reaction, and subsequently titrating with sulfuric acid to determine the consumption of hydroxide ions. The aldehyde content was determined to be 8050 µmol/gram CNCs. The concentration of primary amines in gelatin was determined by the TNBS assay and determined to be 213 µmol/g gelatin. Beta-alanine was used to prepare the calibration curve.

Tuning Hydrogel Precursor Formulation to Obtain Suitable Characteristics:

To achieve accurate control of the properties of the multicellular spheroids in gelatin/a-CNC hydrogels, a set of experimental runs utilizing macroscopic gelatin/a-CNC hydrogels and macroscopic gelatin/a-CNC hydrogels seeded with a suspension of breast cancer cells (MCF-7) were performed. For the macroscopic gelatin/a-CNC hydrogels seeded with a suspension of b MCF-7 cells, the set of experimental runs utilized the suspension of MCF-7 cells having a cell concentration of $3.4 \times 10^7$ cell/mL in a precursor solution of a-CNCs and gelatin.

The characterization and optimization of hydrogel formulations are performed using macroscopic hydrogels and by analyzing the hydrogels using scanning electron microscopy (SEM) imaging, rheometry, swelling, mechanical characterization, gelation time characterization, permeability experiments.

Mechanical Characterization:

The Young's modulus of the hydrogels was determined in cyclic compression experiments using a Mach-1 Mechanical tester (Biomomentum Inc., QC) operating in parallel plate geometry. The hydrogel disks for mechanical testing were 3.25 mm in height and 14 mm in diameter. The disks were compressed by applying 20% strain in the z-direction at a rate of 0.03 mm/s. The Young's modulus of the hydrogels was determined by fitting the linear portion of the resulting stress-strain curve. All hydrogels were equilibrated for 24 h before the measurements.

Figure 5:
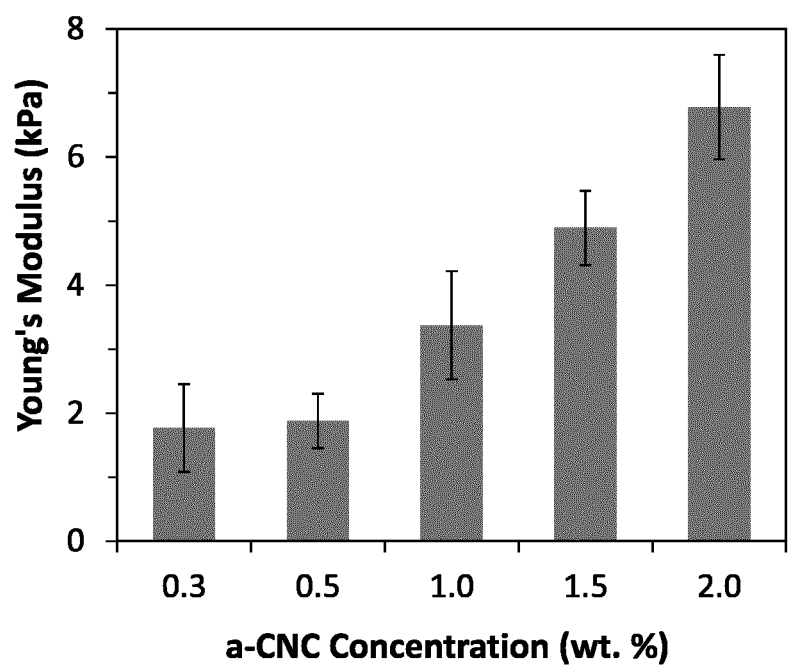
FIG. 5 shows the variation in the Young's modulus of a-CNC/gelatin hydrogels with varying the concentration of a-CNCs.

FIGS. 5 and 6 show the variation in the Young's modules of a-CNC gelatin hydrogels with varying concentration of a-CNCs and a gelatin concentration of 2 wt %. As the concentration of a-CNC increases the hydrogel stiffness also increases from 1.8±0.7 kPa for 0.3 wt % of a-CNC to 6.8±0.8 kPa for 2.0 wt %.

Figure 25:
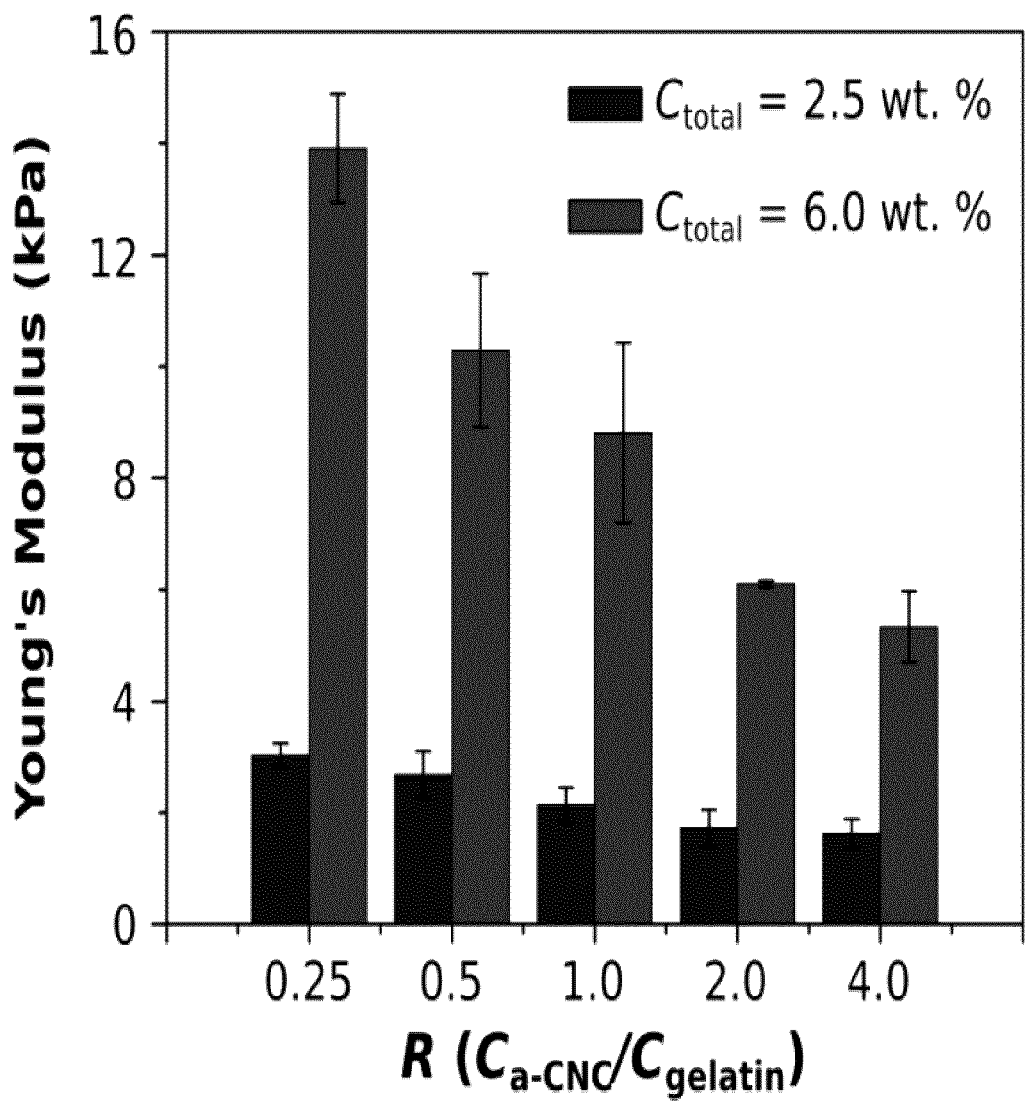
FIG. 25 shows the effect of varying R on the hydrogel's Young's modulus at $C_{total}$ of 2.5 and 6.0 wt %.

FIG. 25 shows the effect of varying R on the hydrogel's Young's modulus at $C_{total}$ of 2.5 and 6.0 wt %.

Hydrogel Permeability Characterization:

The hydrogel permeability was characterized by using the experimental setup as described by Prince et al. To determine Darcy permeability of the a-CNC/gelatin hydrogels, a hydrogel sample with the dimensions 3 mm×3 mm×13.7 mm (width×height×length) was formed in a chamber fabricated in poly(dimethylsiloxane) (PDMS). Perfluoroalkoxyalkane tubing (IDEX Health & Science) was used to connect the ends of the chamber to inlet and outlet reservoirs containing HBSS solution. A pressure difference was applied across the hydrogel by varying the height of the inlet reservoir relative to that of the outlet reservoir. The HBSS solution was under the influence of the pressure drop. The value of the volumetric flow rate (Qp) of the HBSS solution perfused through the hydrogel sample was determined by measuring the change in the mass of the outlet reservoir over a particular time interval. The Darcy permeability was determined as:

$$K_s = \frac{\eta L Q_p}{A \Delta P}$$

where A is the hydrogel's cross-sectional area (9 mm$^2$), L is the hydrogel length(=13.7 mm), ΔP is the pressure drop across the hydrogel, and η is the viscosity of HBSS solution (taken as 1.002 cP, the viscosity of water at room temperature).

A hydrogel sample was prepared in a chamber with dimensions 3 mm×3 mm×13.7 mm (width×height×length), which was fabricated from poly(dimethyl siloxane) (PDMS). The two openings of the chamber were connected to an inlet and outlet reservoir, each containing 10 mL of HBSS. Perfluoroalkoxyalkane tubing (IDEX Health & Science) was used to connect the ends of the chamber to inlet and outlet reservoirs containing HBSS. A pressure difference was applied across the hydrogel by varying the height of the inlet reservoir relative to that of the outlet reservoir. To ensure that the pressure drop, ΔP, applied to the hydrogel does not lead to a substantial change in hydrogel structure, we ensured that a linear relationship exists between the ΔP and volumetric flow rate in the range 1500≤ΔP≤3490 Pa for hydrogels, as expected for a porous network with a static structure.

Figure 7:
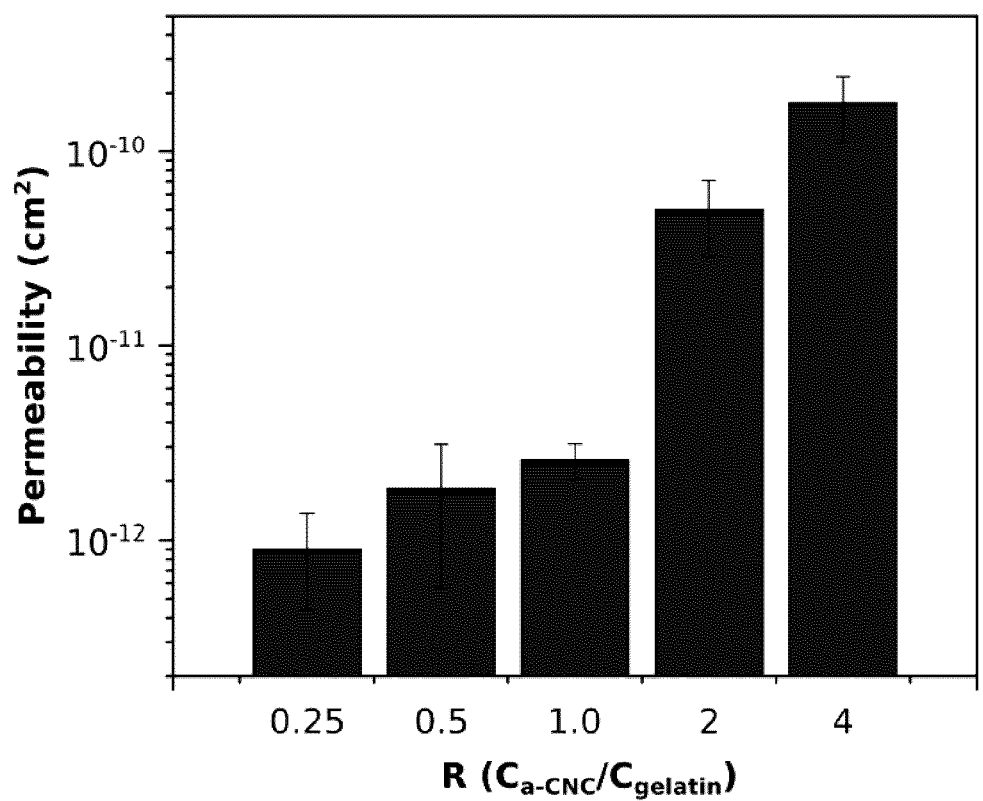
FIG. 7 shows the variation in the Darcy permeability of the hydrogel used for cell culture when changing the concentration ratio of a-CNC-to-gelatin™. The total concentration of the hydrogel ($C_{a\text{-}CNC}+C_{gelatin}$) was 2.5 wt. %.

FIG. 7 shows the variation in the Darcy permeability of the hydrogel used for cell culture. The total concentration of the hydrogel ($C_{a-CNC}+C_{gelatin}$) was 2.5 wt %. The permeability increases as the a-CNC-to-gelatin ratio® increases. The change in permeability increased over 3 orders of magnitude by varying R from 0.25 to 4.

Figure 26:
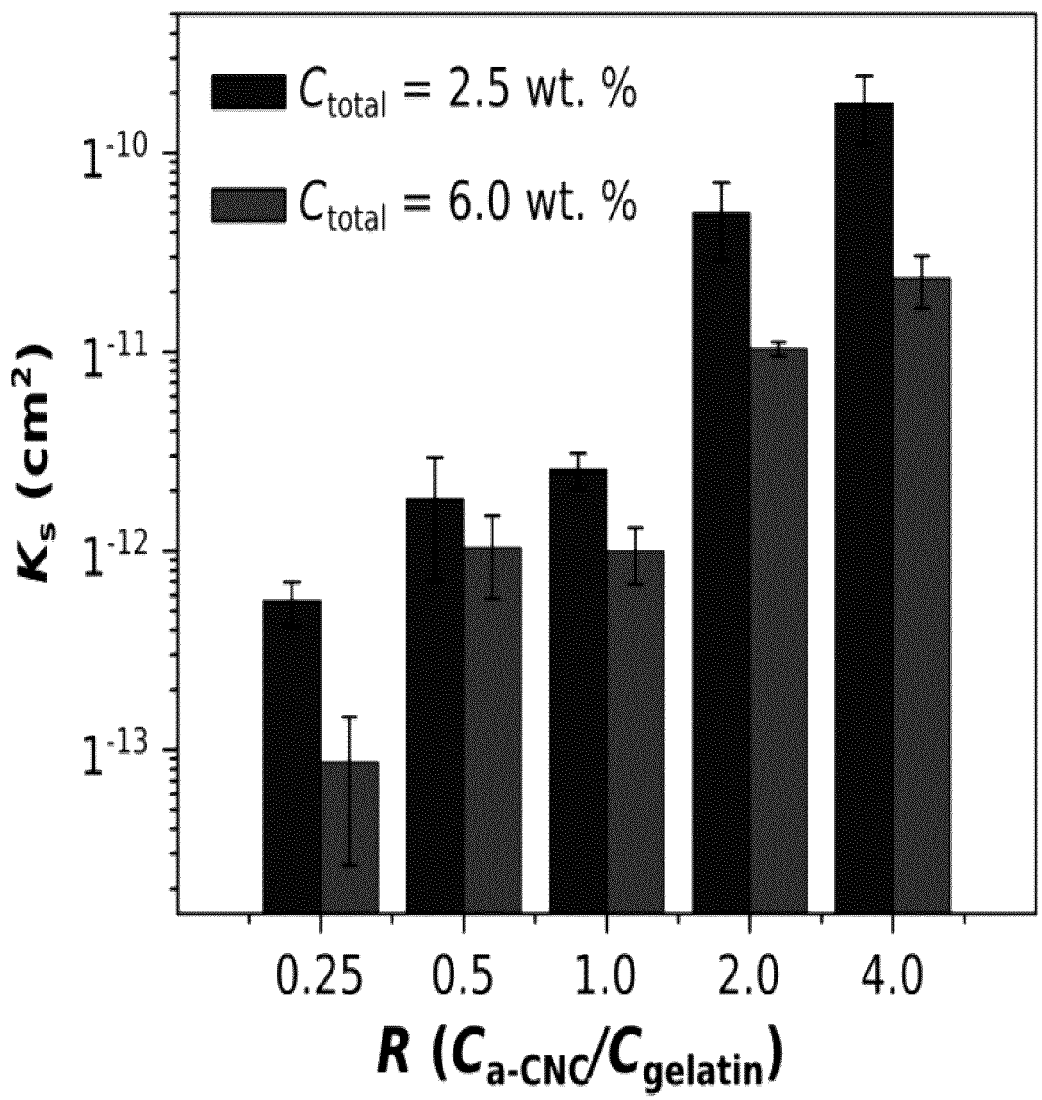
FIG. 26 shows the variation in hydrogel permeability with varying R, at $C_{total}$ of 2.5 and 6 wt %.

FIG. 26 shows the variation in hydrogel permeability with varying R, at $C_{total}$ of 2.5 and 6 wt %.

Figure 24:
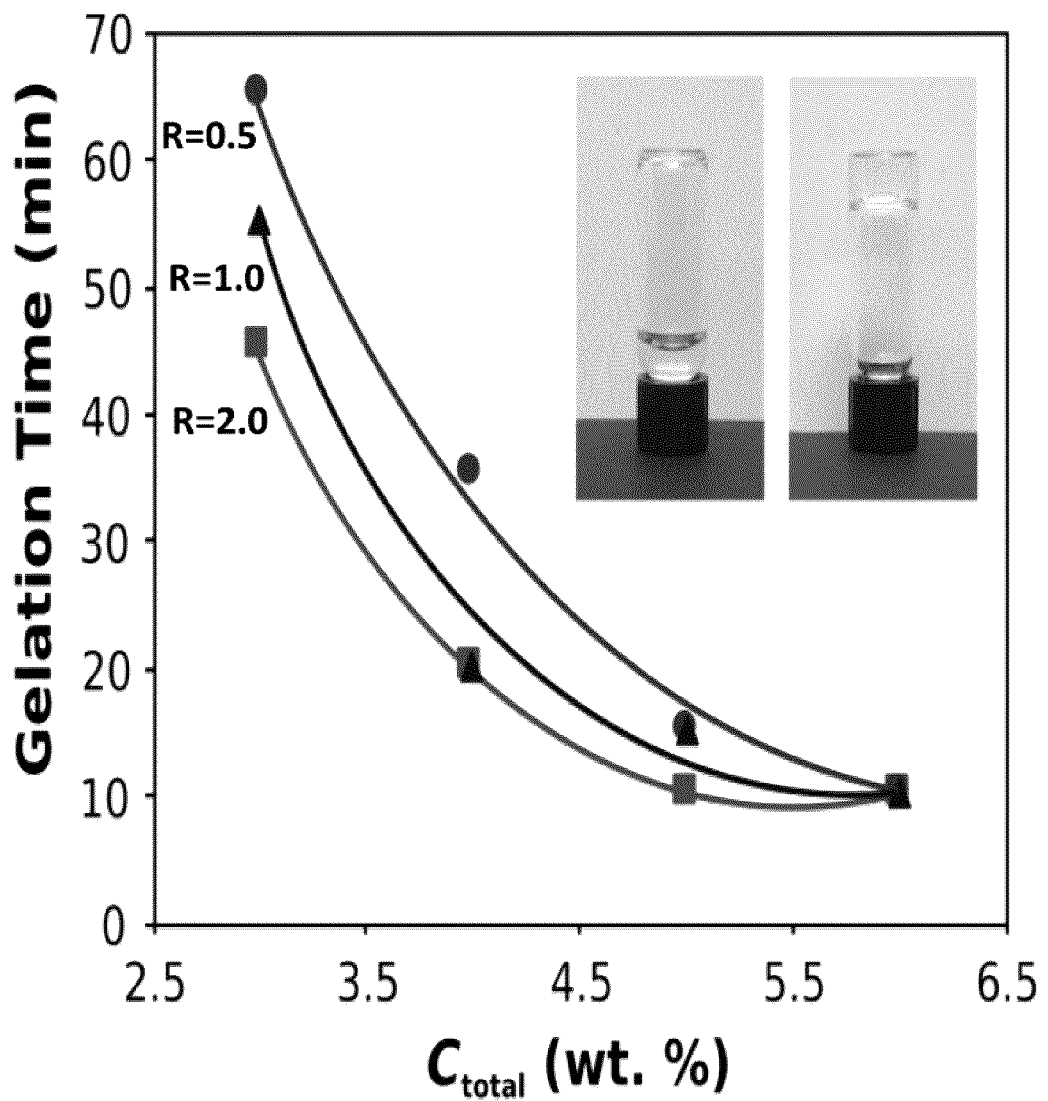
FIG. 24 shows the dependence of gelation time on $C_{total}$ at R=0.5 (●), R=1.0 (▲), and R=2.0 (■). Inset: picture of an a-CNC/gelatin hydrogel before (left) and after gelation (right).

Determination of Gelation Time:

The gelation time for macroscopic a-CNC/gelatin hydrogels was determined by the inversion test. A 1 mL vial containing 500 μL of the mixed suspension of a-CNCs and gelatin was inverted every 5 min at room temperature. Gelation time was determined as the time when no flow was observed upon inversion. The variation in gelling time is achieved by varying the gelatin-to-a-CNC concentration ratio and additionally, by varying the total concentration of a-CNCs and gelatin. As shown in FIG. 24, the gelation time vary depending on the ratio gelatin-to-a-CNC ratio and the total concentration of a-CNCs and gelatin. FIG. 24 shows that it is possible, with the exemplified formulations, to tune the gelation time between about 10 min. to almost to 70 min.

According to an embodiment, for the purpose of preparing multicellular spheroids in a-CNCs/gelatin hydrogels using a microfluidic device, it was found that the concentration of gelatin and the ratio of concentrations of a-CNCs and gelatin in the solution may be varied such that the time required for the formation of the hydrogel was tuned to be anywhere between about 10 minutes to hours but preferably between about 30 minutes to about 1.5 hours, and more preferably from about 1 to about 1.5 hours. Although longer gelation time may be possible, it will be appreciated that gelation times which are too long may be problematic and/or not suitable due to cell death.

Furthermore, when a-CNCs/gelatin hydrogels are used for the preparation of multicellular spheroids using a microfluidic device, the gelation time was controlled by changing the total concentration of a-CNCs and gelatin and the mass ratio of a-CNCs-to-gelatin to optimize the formation of droplets before a significant increase in viscosity (taking ~1 h).

Cell Culture:

Prior to the preparation of the macroscopic a-CNC/gelatin hydrogels seeded with human breast cancer MCF-7 cells, the cells were cultured in 250 mL polystyrene tissue culture flasks. To each flask, 10 mL of Dulbecco's Modified Eagle Medium with 4.5 g/L glucose, L-glutamine, and sodium pyruvate (DMEM-F12, GIBCO), supplemented with 10% (v/v) fetal bovine serum (FBS, Invitrogen), and 1% (v/v) penicillin/streptomycin were added. The flasks were incubated at 37° C. with a constant 5% CO2 supply in the incubator. For cell passage, a Trypsin-EDTA solution (0.25 wt %, GIBCO) was used to detach cells from the basement support. After detachment, 5 mL of fresh media was added and the suspension was centrifuged at 184×g and 20° C. for 3 min. The supernatant was removed, and the pellet was resuspended in 1 mL fresh media. 300 μL of the cell suspension was then transferred to fresh media in a new flask. Cells were passaged every 5 days.

Preparation of the Macroscopic a-CNC/Gelatin Hydrogels Seeded with Human Breast Cancer MCF-7 Cells:

Prior to the preparation of the macroscopic a-CNC/gelatin hydrogels seeded with human breast cancer MCF-7 cells, an a-CNC suspension at a selected concentration and a gelatin solution at a selected concentration were prepared in Hank's balanced salt solution (HBSS) in order to obtain a a-CNC/gelatin hydrogel with a desired final wt % concentration of a-CNC and gelatin. Both solutions were sterilized by exposure to ultraviolet light (Sterilaire Lamp, 254 nm, 345 μW/cm2) for 5 min. The gelatin solution and a-CNC suspension were then mixed with a cell suspension to give the final hydrogel composition. The cell density was 500 cells/well. Cells were cultured in a 96-well plate and incubated at 37° C. at a constant 5% CO2 supply for 24 h before adding an additional 100 μL of fresh media to each well.

For example, prior to the preparation of the macroscopic a-CNC/gelatin hydrogels seeded with human breast cancer MCF-7 cells, a 3 wt % a-CNC suspension and a 10 wt % gelatin solution were prepared in Hank's balanced salt solution (HBSS). Both solutions were sterilized by exposure to ultraviolet light (Sterilaire Lamp, 254 nm, 345 μW/cm2) for 5 min. The gelatin solution and a-CNC suspension were then mixed with a cell suspension to give a final hydrogel composition of $C_{total}$=3 wt %, $C_{gelatin}$=2 wt % and $C_{a\text{-}CNC}$=1 wt % (weight ratio of a-CNC to gelatin® is 0.5). The cell density was 500 cells/well. Cells were cultured in a 96-well plate and incubated at 37° C. at a constant 5% CO2 supply for 24 h before adding an additional 100 µL of fresh media to each well.

Live/Dead Assay and Fluorescence Staining:

On day 1, 8, and 21 of cell culture, the cells were stained with calcein-AM (Invitrogen, Carlsbad; green fluorescence) and ethidium homodimer-1 (Invitrogen, Carlsbad; red fluorescence) to identify live versus dead cells. To each well, 100 µL of the assay solution was added and incubated for 45 min at 37° C. The cells were then imaged by fluorescence microscopy (Nikon, Eclipse Ti).

Figure 8:
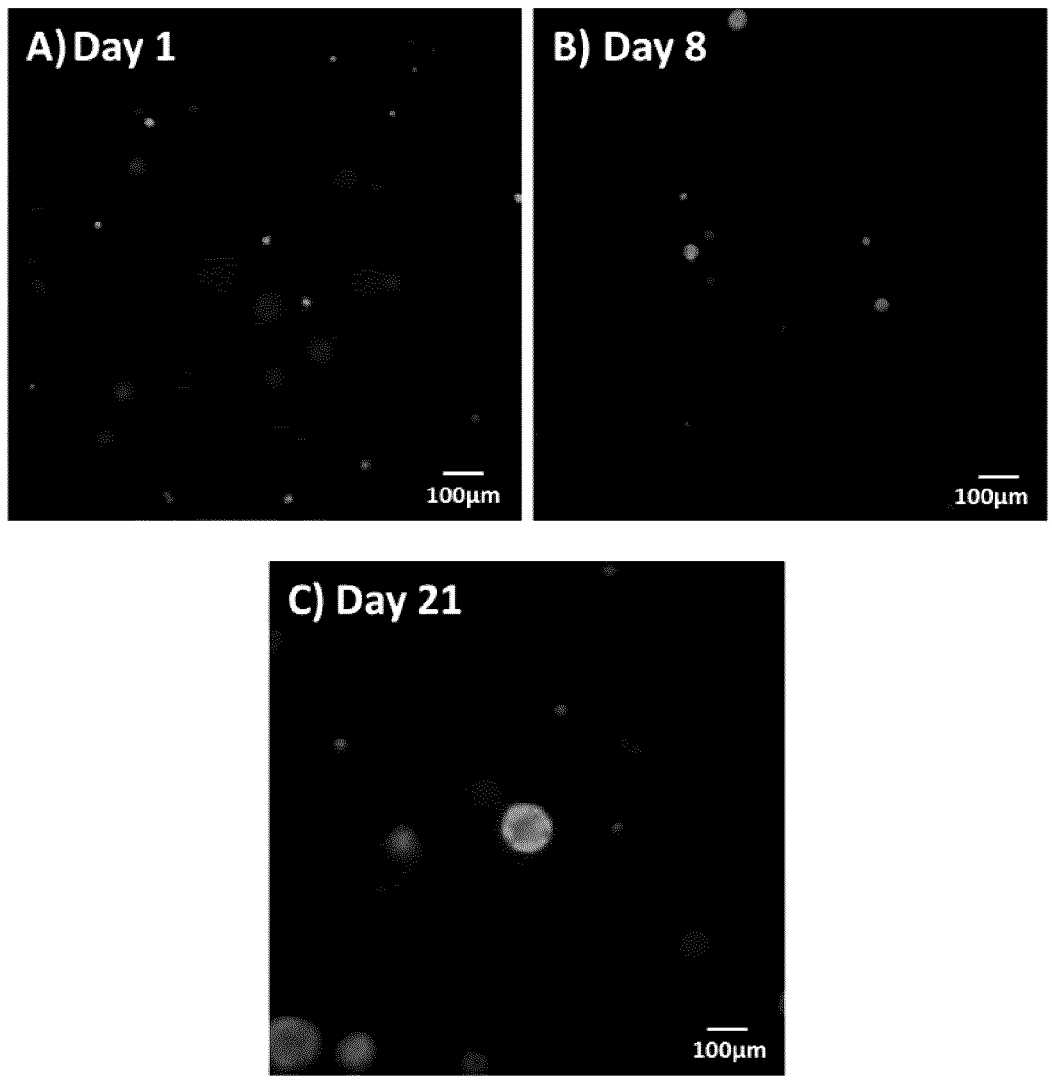
FIG. 8 shows the viability and MCF growth from MCF-7 cells in the hydrogels with a-CNC concentration of 1 wt % and gelatin concentration of 2 wt % after A) 1 day, B) 8 days and C) 21 days (Scale bars: 100 µm).

FIG. 8 shows the viability and MCF growth from MCF-7 cells in the hydrogels with a-CNC concentration of 1 wt % and gelatin concentration of 2 wt % after A) 1 day, B) 8 days and C) 21 days.

Figure 9:
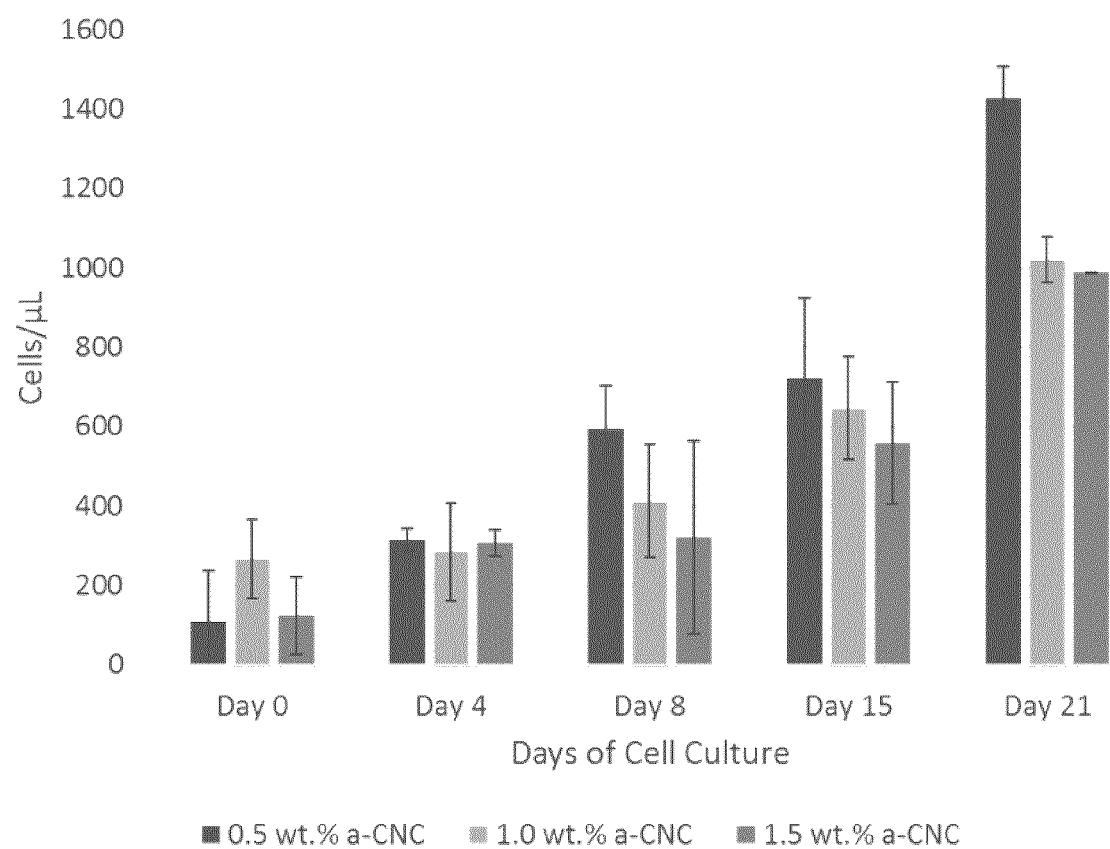
FIG. 9 shows cell viability of MCF 7 cells over 21 days of cell culture in a-CNC/gelatin hydrogels with different a-CNC concentrations and a gelatin concentration of 2 wt %.

FIG. 9 shows cell viability assay over a period of 21 days using 0.5 wt %, 1.0 wt % and 1.5 wt % a-CNC and a gelatin concentration of 2.0 wt %. A fluorescent colorimetric dye Alamar blue was used to assess metabolic cell activity and cell viability. As seen in FIG. 9, the cell viability is significantly greater at 21 days for hydrogel formulations of 0.5 wt % a-CNC and 2.0 wt % gelatin.

Figure 10:
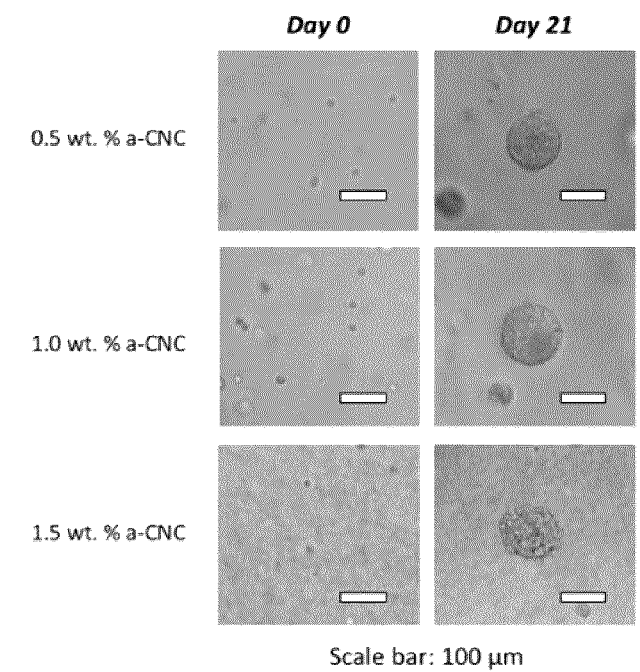
FIG. 10 shows the variation in MCF growth from MCF 7 cells in hydrogels over a period of 21 days with varying a-CNCs and a gelatin concentration of 2 wt %.
Figure 10:
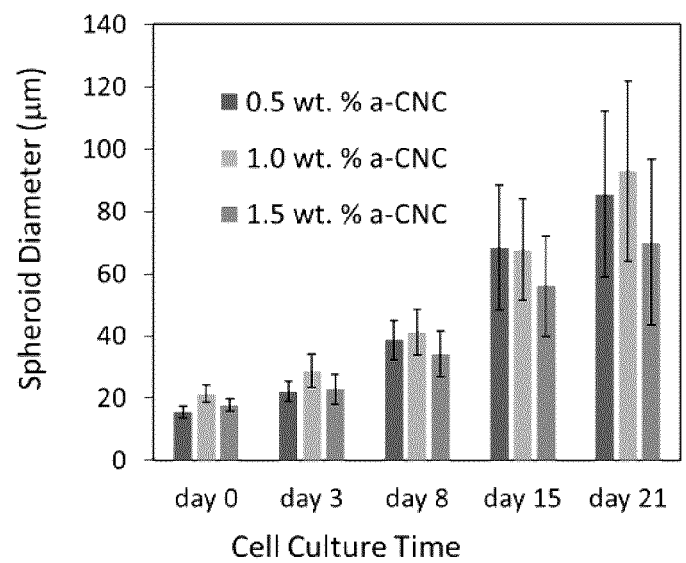

FIG. 10 shows the MCS obtained with MCF 7 cells from 0 day to 21 days with different concentration of a-CNCs and a gelatin concentration of 2 wt %. The variation in MCS diameter with time in hydrogels with varying concentration of a-CNCs, i.e., 0.5 wt %, 1.0 wt % and 1.5 wt % and a gelatin concentration of 2 wt %. For each a-CNC concentration, MCS showed significant growth for each successive time period ($p<0.005$). On day 15 and day 21, MCS growth from MCF 7 cells in 1.5 wt % was statistically lower compared to 0.5 wt % and 1.0 wt % ($p<0.005$).

Figure 11:
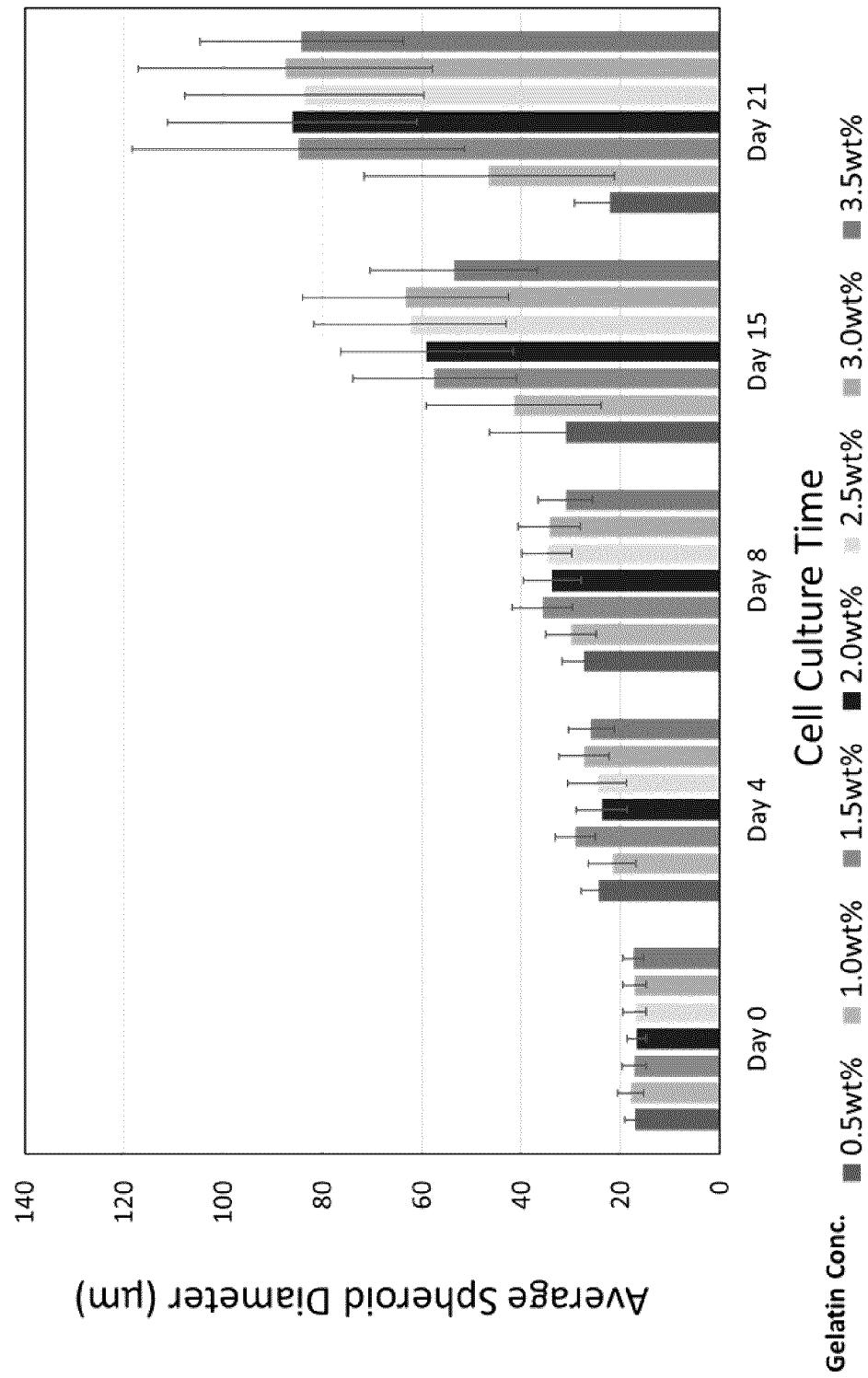
FIG. 11 shows the variation in MCF growth from MCF 7 cells in hydrogels over a period of 21 days with varying gelatin concentration at a-CNC concentration of 1 wt %.

FIG. 11 shows the variation in MCF growth over a period of 21 days from MCF 7 cells in hydrogels with varying gelatin concentration, i.e., 0.5 wt %, 1.0 wt %, 1.5 wt %, 2.0 wt %, 2.5 wt %, 3.0 wt % and 3,5 wt % and a-CNC concentration of 1 wt %. At gelatin concentration of 1.5-3.5 wt % significant MCS growth was observed for each successive time period ($p<0.005$). As seen in FIG. 11, hydrogels with $C_{gelatin}$ above 1.5 wt % were more favorable for MCS growth.

Immunofluorescence Assay:

Immunostaining was used to evaluate the cell-to-cell interactions and cell nuclei organization. After 3 day culture, a-CNC/gelatin hydrogels with-multicellular spheroids formed at a cell concentration of $1.2 \times 10^8$ cell/mL were fixed with 4% paraformaldehyde diluted in HBSS. All the solutions used below were infused into the channels and microwells at a rate of 0.1 mL/h at room temperature. A solution of 4% paraformaldehyde was perfused into the channels and wells for 90 min. Subsequently, the paraformaldehyde solution was washed away by infusing a solution of 0.1 M glycine in HBSS for 90 min. Then, a solution of 0.5% Triton X-100 in HBSS was infused into the channels and wells to permeabilize the cells for 60 min.

To remove excess Triton X-100, the Polymer-multicellular spheroids were washed by a washing solution (IF wash) consisting of 0.05 wt % NaN3, 0.1 wt % Bovine Serum Albumin, 0.2 vol % mL Triton X-100, 0.05 vol % mL Tween 20 in HBSS for 30 min. After that, a block solution (10% goat serum in IF wash) was infused to the channels and wells for 90 min. The block solution was replaced by a solution of the antibody (Alexa Fluor 488 E-Cadherin Rabbit monoclonal antibody, 1:800 dilutions in HBSS, Cell Signaling Technology), which was allowed to incubate overnight at 4° C. To remove antibody excess, the Polymer-multicellular spheroids were perfused with the IF wash for 60 min at room temperature. To stain cell nuclei, 0.5 ng/mL 4',6-diamidino-2-phenylindole (DAPI, Life technologies) in HBSS was perfused into Polymer-multicellular spheroids for 10 min. The structure of CSs was visualized and imaged by Nikon A1 confocal microscope.

Figure 12:
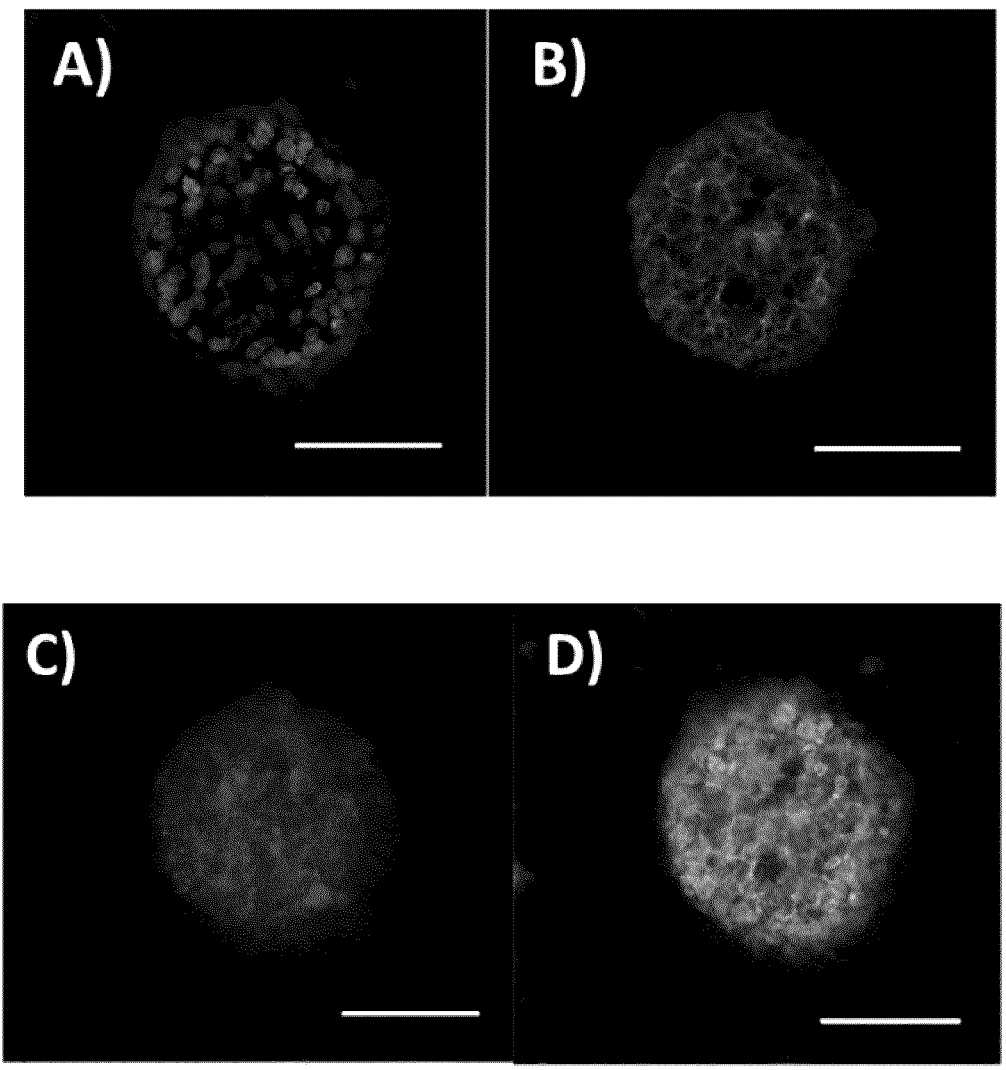
FIG. 12 shows immunofluorescence staining of breast cancer MCS grown from MCF-7 breast cancer cells formed in a-CNC/gelatin with a-CNC/gelatin concentrations of 0.5 wt % and 2 wt. % respectively after 21-day culture. A) Immunostaining of the MCS by DAPI (Blue) B) Immunostaining of the MCS by Alexa Fluor 488 E-Cadherin Rabbit monoclonal antibody (green), C) Immunostaining of the MCS by Alexa Fluor 568 Phalloidin (Red) and D) image of the MCS shown in A), B) and C) (Scale bars are 50 µm).

Immunostaining of the a-CNC/gelatin-multicellular spheroids after 3 day culture was used to evaluate the cell-cell interactions and cell nuclei organization. FIG. 12 shows immunofluorescence staining of breast cancer MCS grown from MCF-7 breast cancer cells formed in a-CNC/gelatin with a-CNC/gelatin concentrations of 0.5 wt % a-CNC and 2 wt. % gelatin after 21-day culture: FIG. 12A) Immunostaining of the MCS by DAPI (Blue); FIG. 12B) Immunostaining of the MCS by Alexa Fluor 488 E-Cadherin Rabbit monoclonal antibody (green); FIG. 12C) Immunostaining of the MCS by Alexa Fluor 568 Phalloidin (Red); and FIG. 12D) merged image composed of the fluorescence images in FIGS. 12A, B and C. The results shown in FIG. 12 indicates that the multicellular aggregates transform from a cluster of cells into cancerous spheroids which may act as cancerous micro-tumors and are likely suitable to screen the effect of drugs on tumors.

Preparation of the Macroscopic a-CNC/Gelatin Hydrogels Seeded with Patient-Derived Pancreatic Cancer Cells:

Prior to the preparation of the macroscopic a-CNC/gelatin hydrogels seeded with patient derived pancreatic cells, the cells were cultured in 50 µL matrigel (8.8-9 mg/mL) domes in a 48 well TC plate. To each well, 1 mL of Advanced Dulbecco's Modified Eagle Medium with 4.5 g/L glucose, L-glutamine, and sodium pyruvate (Advanced DMEM-F12, GIBCO), supplemented with 2 mM GlutaMAX, 10 mM HEPES, 100 U/mL Antibiotic-Antimycotic, 1× B-27 Supplement 1.25 mM N-Acetyl-L-cytseine, 10 nM gastrin (1-14), 50 ng/mL Recombinant Human EGF, 100 ng/mL Recombinant Human Noggin, 100 ng/mL Recombinant Human FGF-10, 0.5 mM A 83-01, 10 mM Y-27632, 10 mM Nicotinamide, 20% v/v Wnt-3a conditioned media, and 30% v/v Human R-Spondin1 conditioned media. The well plates were incubated at 37° C. with a constant 5% CO2 supply in the incubator. For cell passage, 1 mL of a TryLE Express solution (Invitrogen) was used to detach cells and disintegrate the matrigel. After cell release, the suspension was added to 5 mL of fresh media and centrifuged at 250×g and 20° C. for 5 min. The supernatant was removed, and the pellet was resuspended in 1 mL fresh matrigel. 25 µL of the cell suspension was then transferred to a new well plate and 1 mL fresh media was added. Cells were passaged every 5 days.

Prior to the preparation of the macroscopic a-CNC/gelatin hydrogels seeded with patient derived pancreatic cells, a 3 wt % a-CNC suspension and a 10 wt % gelatin solution were prepared in Hank's balanced salt solution (HBSS). Both solutions were sterilized by exposure to ultraviolet light (Sterilaire Lamp, 254 nm, 345 µW/cm2) for 5 min. The gelatin solution and a-CNC suspension were then mixed with a cell suspension to give a final hydrogel composition of Ctotal=3 wt %, Cgelatin=2 wt % and Ca CNC=1 wt % (weight ratio of a-CNC to gelatin® is 0.5). The cell density was 500 cells/well. Cells were cultured in a 96-well plate and incubated at 37° C. at a constant 5% CO2 supply for 24 h before adding an additional 100 µL of fresh media to each well.

Figure 13:
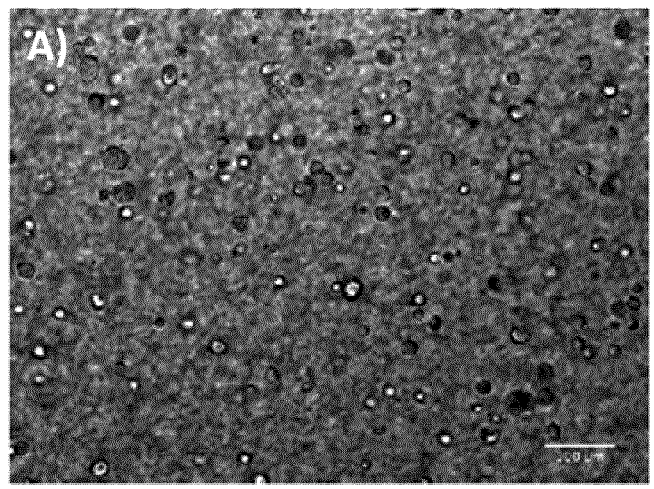
FIG. 13 shows the viability of patient-derived pancreatic cancer cells on Day 1 in the hydrogel with a-CNC and gelatin concentrations of 0.5 and 2 wt. %, respectively. The cells were stained by calcein AM (green) and Ethidium homodimer-1 (red). Green color and lack of red color signify high cell viability in the hydrogel (Scale bars are 20 µm).
Figure 13:
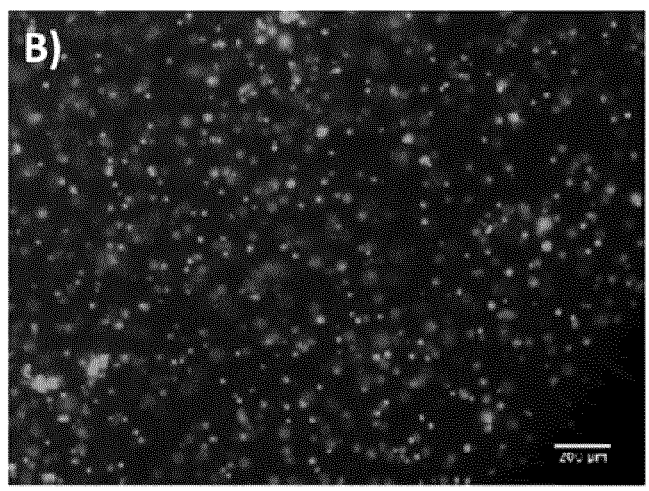

FIG. 13 shows the viability of patient-derived pancreatic cancer cells on Day 1 in the hydrogel with 0.5 wt % a-CNC and 2 wt. %, gelatin. The cells were stained by calcein AM (green) and Ethidium homodimer-1 (red). Green color and lack of red color signify high cell viability in the hydrogel.

Figure 14:
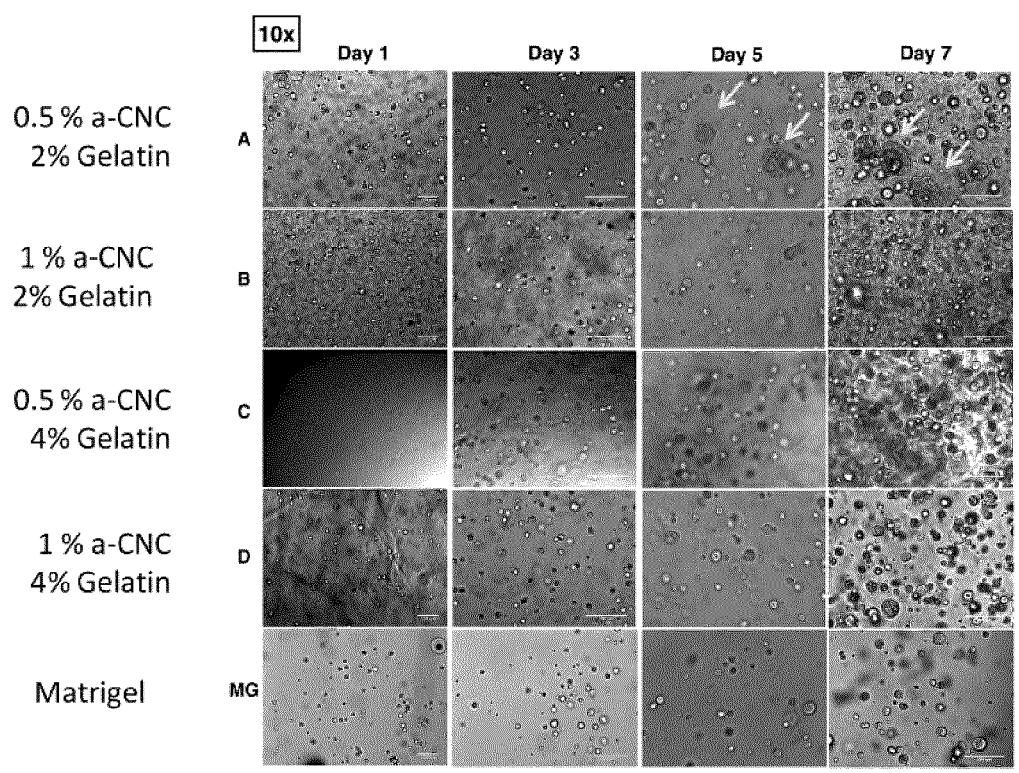
FIG. 14 shows the culture of primary pancreatic organoids in a-CNC/gelatin hydrogel with varying compositions.

FIG. 14 shows the culture of primary pancreatic organoids in a-CNC/gelatin hydrogel with varying compositions compared to matrigel. The arrows show the presence of large cancer spheroids at days 5 and 7 for 0.5 wt % a-CNC and 2 wt % gelatin indicating that the hydrogels may be tuned for different cells.

Preparation of the Macroscopic a-CNC/Gelatin Hydrogels Seeded with Patient-Derived Breast Cancer Cells:

Breast cancer cells were obtained from dissociated tissue prior to the preparation of the macroscopic a-CNC/gelatin hydrogels seeded with patient-derived breast cancer.

Prior to the preparation of the macroscopic a-CNC/gelatin hydrogels seeded with patient-derived breast cancer cells, the cells were cultured in 50 µL matrigel (8.8-9 mg/mL) domes in a 48 well TC plate. To each well, 1 mL of Advanced Dulbecco's Modified Eagle Medium with 4.5 g/L glucose, L-glutamine, and sodium pyruvate (Advanced DMEM-F12, GIBCO), supplemented with 2 mM Gluta-MAX, 10 mM HEPES, 100 U/mL Antibiotic-Antimycotic, 1> B-27 Supplement 1.25 mM N-Acetyl-L-cytseine, 10 nM gastrin (1-14), 50 ng/mL Recombinant Human EGF, 100 ng/mL Recombinant Human Noggin, 100 ng/mL Recombinant Human FGF-10, 0.5 mM A 83-01, 10 mM Y-27632, 10 mM Nicotinamide, 20% v/v Wnt-3a conditioned media, and 30% v/v Human R-Spondin1 conditioned media. The well plates were incubated at 37° C. with a constant 5% CO2 supply in the incubator. For cell passage, 1 mL of a TryLE Express solution (Invitrogen) was used to detach cells and disintegrate the matrigel. After cell release, the suspension was added to 5 mL of fresh media and centrifuged at 250×g and 20° C. for 5 min. The supernatant was removed, and the pellet was resuspended in 1 mL fresh matrigel. 25 µL of the cell suspension was then transferred to a new well plate and 1 mL fresh media was added. Cells were passaged every 5 days.

Prior to the preparation of the macroscopic a-CNC/gelatin hydrogels seeded with patient-derived breast cells, a 3 wt % a-CNC suspension and a 10 wt % gelatin solution were prepared in Hank's balanced salt solution (HBSS). Both solutions were sterilized by exposure to ultraviolet light (Sterilaire Lamp, 254 nm, 345 µW/cm2) for 5 min. The gelatin solution and a-CNC suspension were then mixed with a cell suspension to give a final hydrogel composition of Ctotal=3 wt %, Cgelatin=2 wt % and Ca CNC=1 wt % (weight ratio of a-CNC to gelatin® is 0.5). The cell density was 500 cells/well. Cells were cultured in a 96-well plate and incubated at 37° C. at a constant 5% CO2 supply for 24 h before adding an additional 100 µL of fresh media to each well.

Figure 15:
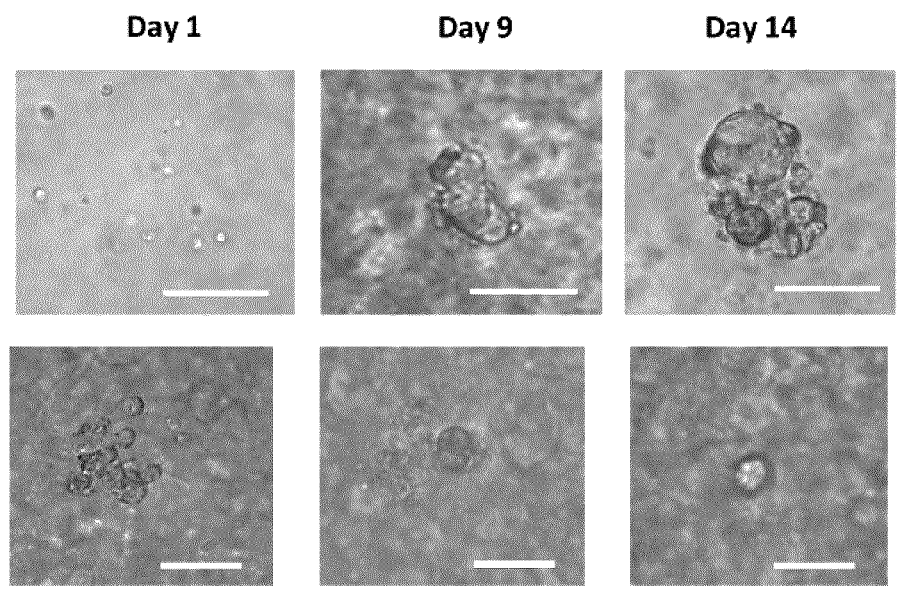
FIG. 15 shows the growth of multicellular cancer spheroids from breast tumor biopsy at A) day 1, B) Day 9 and C) Day 14 (Images are taken from the same location in the hydrogel on chip. a-CNC and gelatin concentrations are 0.5 and 2 wt. %, respectively) and D-F) different views of MCSs grown from breast cancer patient-derived cells in the a-CNC/gelatin hydrogel after day 8 (the concentration of a-CNCs and gelatin are 0.5 and 2 wt. %, respectively) (Scale bars are 50 µm).

FIG. 15 shows the growth of multicellular cancer spheroids from breast tumor biopsy at A) day 1, B) Day 9 and C) Day 14 (Images were taken from the same location in the hydrogel). The hydrogels contain 0.5 wt % a-CNC and 2 wt % gelatin. and D-F) different views of MCSs grown from breast cancer patient-derived cells in the a-CNC/gelatin hydrogel after day 8 (the concentration of a-CNCs and gelatin are 0.5 and 2 wt. %, respectively).

Figure 17:
FIG. 17 shows the viability of MCF 7 breast cancer cells on Day 1 on the microfluidic device in the hydrogel with a-CNCs and gelatin concentrations of 0.5 and 2 wt. %, respectively (brightfield image (left) and fluorescence microscopy image (right) of the fragment of microfluidic device with cell-laden hydrogels. The cells were stained by calcein AM (green) and Ethidium homodimer-1 (red). Green color and lack of red color signify high cell viability in the hydrogel on the microfluidic device (Scale bars are 200 µm).
Figure 17:
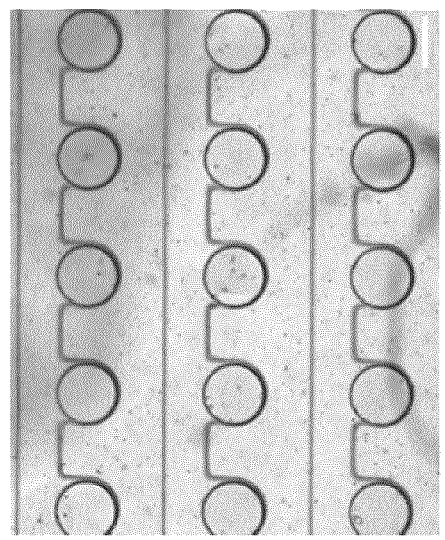
Figure 18:
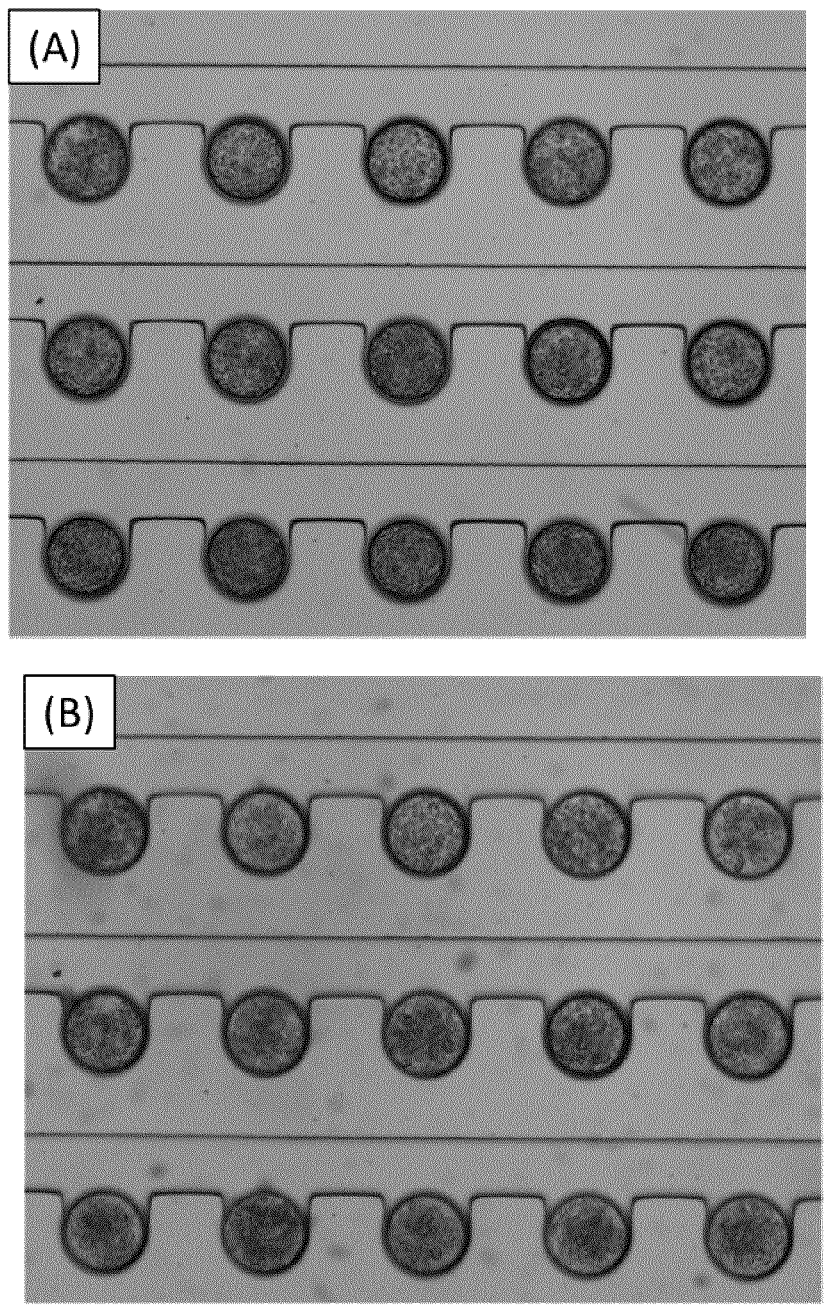
FIG. 18 shows spheroids formed from a high-density of MCF-7 cells laden in agarose microgels. (A) Droplets of high density MCF-7 cell suspension (60%) in agarose solution at 37° C. The droplets are suspended in fluorinated oil. (B) Agarose microgels laden with MCF-7 cells (60%) in media after 1 day of cell culture.
Figure 19:
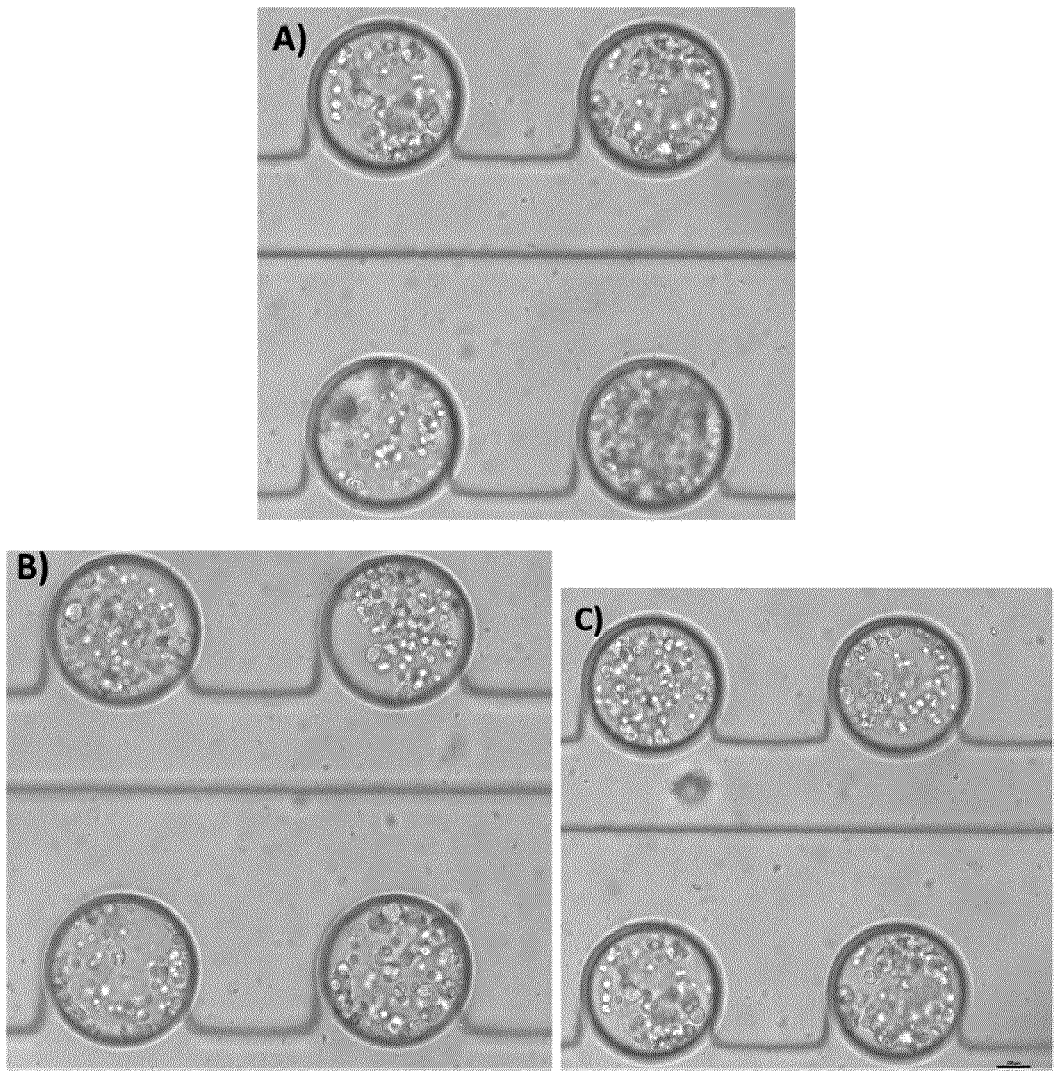
FIG. 19 shows brightfield images of high density spheroids formed by MCF 7 cells in the a-CNC/gelatin hydrogel on day 1. $C_{acNc}$=0.75 wt. %, $C_{gelatin}$=2 wt. %, flow rate=0.02 mL/h (Scale bar is 200 µm).
Figure 20:
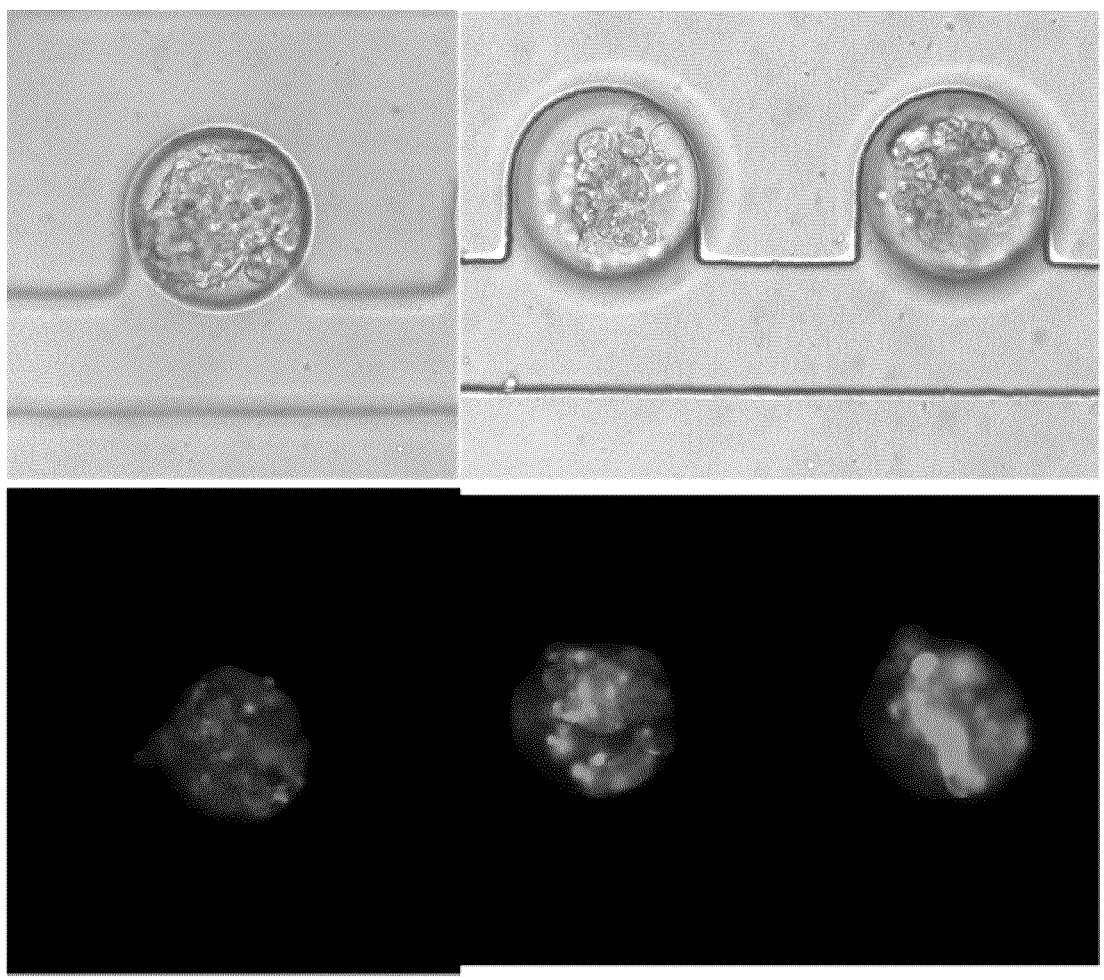
FIG. 20 shows brightfield and florescence images of high-density spheroids formed by MCF 7 cells in the a-CNC/gelatin hydrogel on day 1. $BC_{aCNC}$=0.75 wt. %, $C_{gelatin}$=2 wt. %, flow rate=0.02 mL/h (Scale bar is 200 µm).
Figure 21:
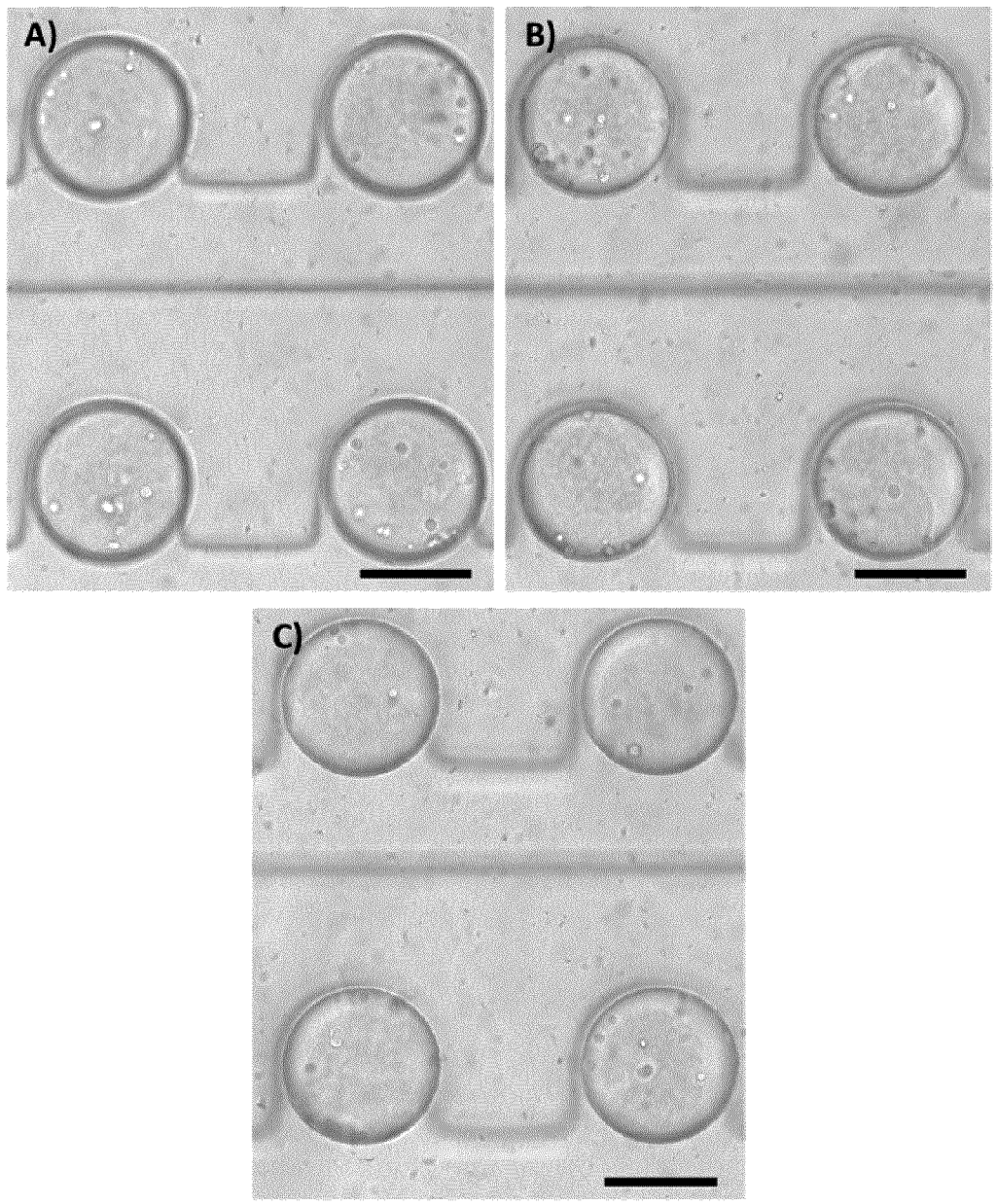
FIG. 21 shows brightfield images of low-density spheroids formed by MCF 7 cells in the a-CNC/gelatin hydrogel on day 1. $C_{acNc}$=0.75 wt. %, $C_{gelatin}$=2 wt. %, flow rate=0.02 mL/h (Scale bar is 200 µm).
Figure 22:
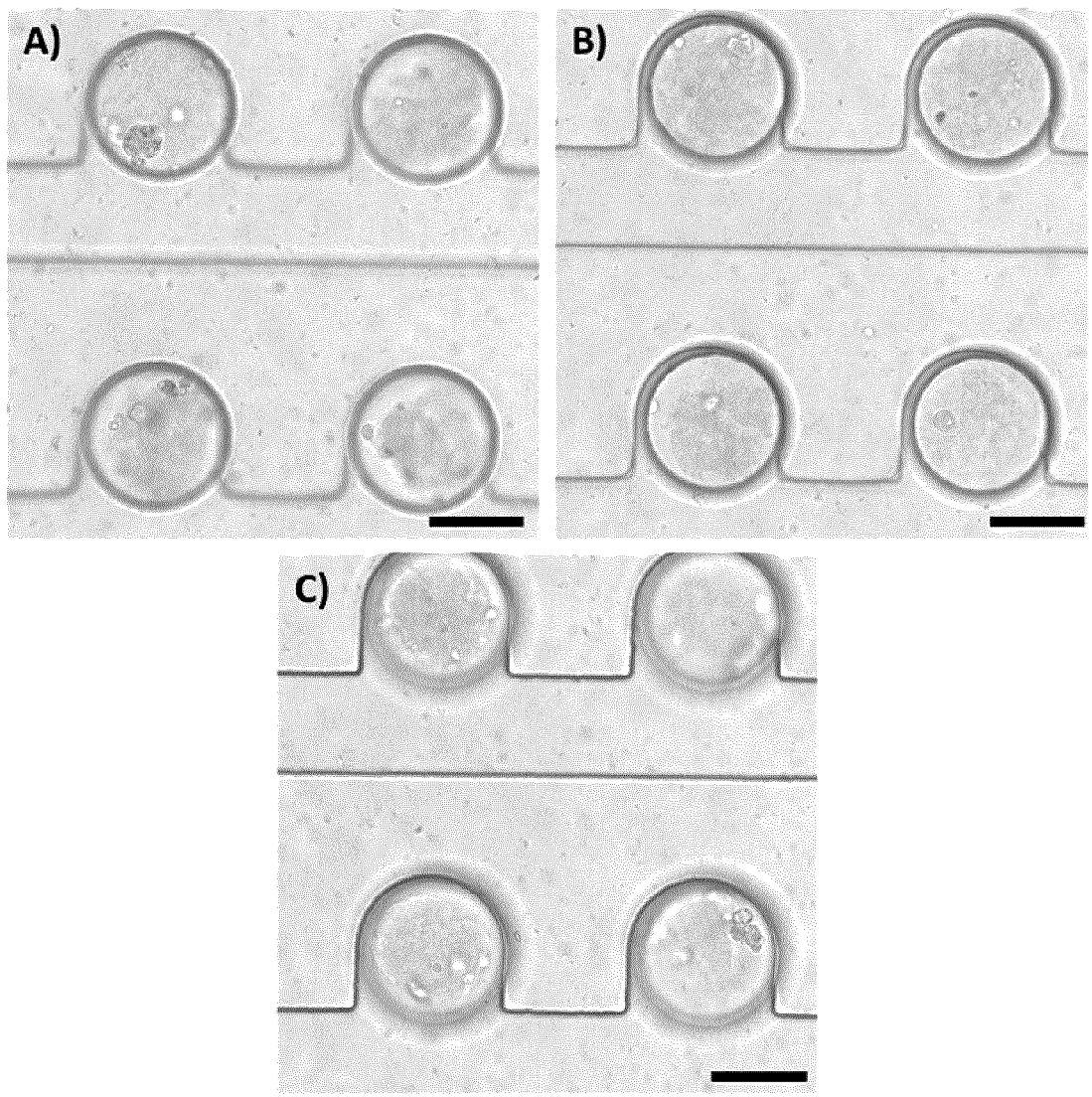
FIG. 22 shows brightfield images of low-density spheroids formed by MCF 7 cells in the a-CNC/gelatin hydrogel on day 7. $C_{acNc}$=0.75 wt. %, $C_{gelatin}$=2 wt. %, flow rate=0.02 mL/h (Scale bar is 200 µm).
Figure 23:
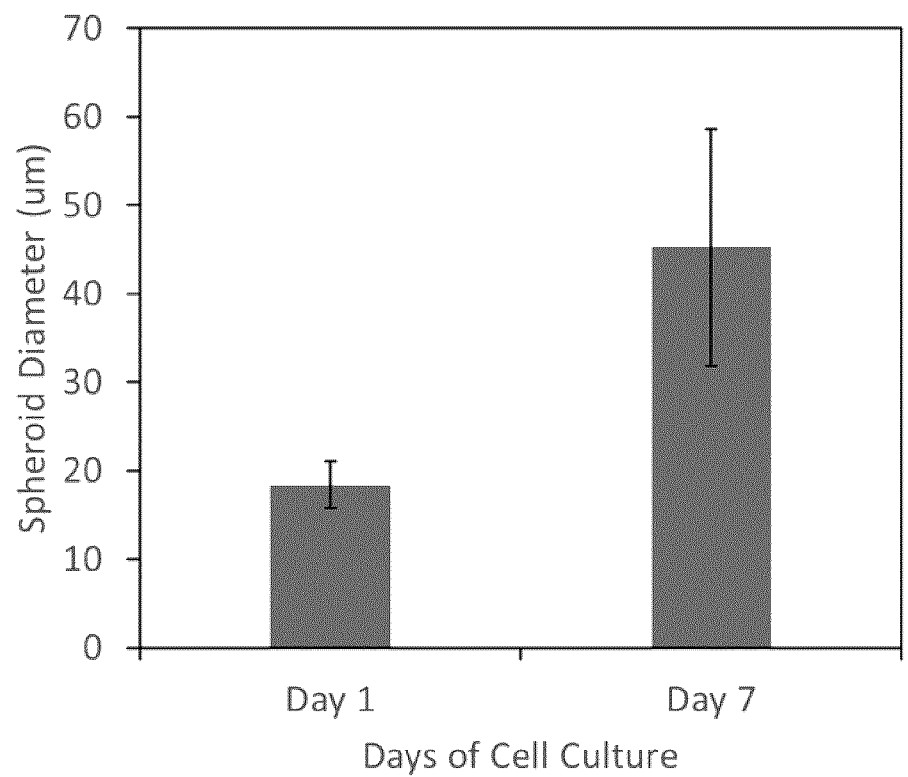
FIG. 23 shows growth profile of low-density spheroids formed by MCF 7 cells in aCNC/gelatin hydrogels in the microfluidic device. $C_{acNc}$=0.75 wt. %, $C_{gelatin}$=2 wt. %, flow rate=0.02 mL/h.

The results obtained with the breast cancer MCF 7 cells, the patient-derived pancreatic cancer cells and the patient-derived breast cancer cells indicate that the hydrogels may be tuned to have suitable characteristics to promote the formation of multicellular aggregates such as multicellular spheroids or organoids using the method, system and device of the present disclosure. Preparation of multicellular aggregates using a microfluidic device:

The microfluidic device 10 disclosed herein may be used in the formation of multicellular aggregates within a hydrogel scaffold (FIGS. 2A, 2B and 2C). According to an embodiment, MCF-7 breast cancer cell suspension was used to obtain cancer spheroids within an a-CNC/gelatin hydrogel droplets as shown in FIGS. 16, 17 and 18.

In a first time, the surface of the microwells 16 and supplying channels 14 was first treated with fluorinated oil mixed with 0.5 wt. % block copolymer perfluorinated polyether-b-(polypropylene glycol-polyethylene glycol-polypropylene glycol)-b-perfluorinated polyether. Next, the supplying channel 14 and microwells 16 is filled with a suspension of MCF-7 breast cancer cells in the precursor solution of gelatin and a-CNCs. The MCF-7 breast cancer cells suspension has a concentration of 1000 cells/µl for the low-density spheroids and $3\times10^7$ cells/µl for high-density spheroids and 2 wt. % gelatin and 0.5 wt. % a-CNC. In the following step, the solution of cells/precursor in the supplying channel 14 is displaced with the fluorinated oil mixture while the solution of cells/precursor is retained in the microwells 16. This step leads to the formation of an array of cell-laden droplets 24. After 1-1.5 h, the precursor gelatin/a-CNC solution in the microwells 16 is transformed in a hydrogel 27 and the fluorinated oil mixture in the supplying channel 14 is replaced with the cell culture medium to induce cell growth and formation of multicellular spheroids.

The growth of the MCF-7 breast multicellular spheroids is stimulated by placing the microfluidic device at 37° C. in an incubator. During incubation, the supplying channels 14 are supplied with a constant flow of the cell nutrition medium. The breast cancer cell viability and the progression of MCS formation are then tested through performing a variety of imaging steps, where the steps include the dyeing and fluoroscopic imaging of the cell cultures in the microwells, after various time exposure to the nutrition medium.

Figure 16:
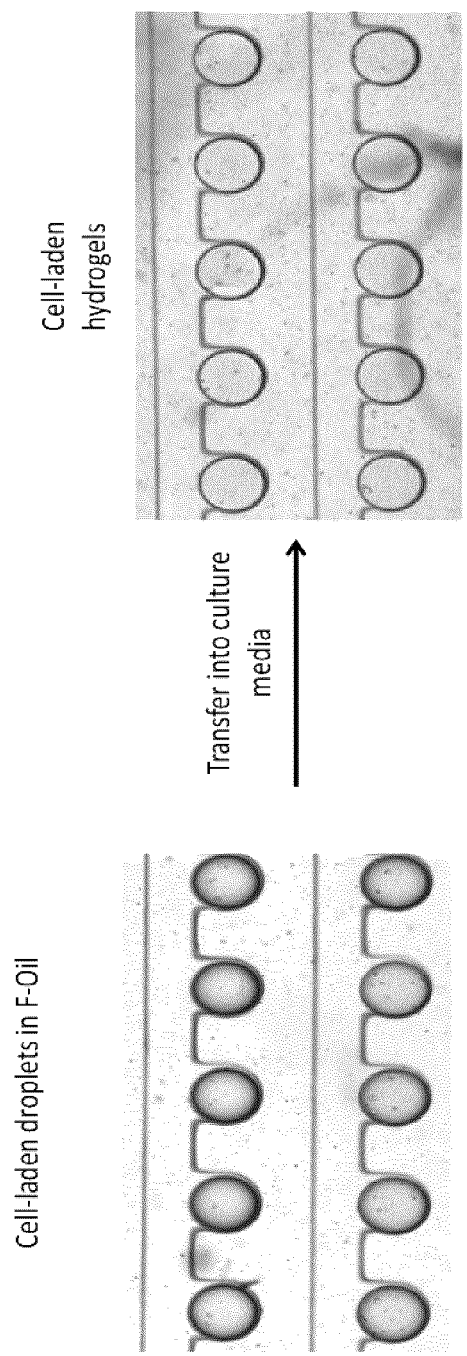
FIG. 16 shows microfluidic preparation of MCF 7 laden a-CNC/gelatin microgels (hydrogel Composition: 0.75 wt. % a-CNC, 2 wt. % gelatin).

FIG. 16 shows the microfluidic preparation of MCF 7 laden a-CNC/gelatin microgels with a composition of 0.75 wt. % a-CNC, 2 wt. % gelatin and an initial cell concentration of 1000 cells/µl for the hydrogel precursor solution.

FIG. 17 shows the viability of MCF 7 breast cancer cells on Day 1 in a-CNC/gelatin microgels with 0.5 wt % a-CNC and 2 wt. % gelatin. The left image corresponds to the brightfield image and the right image correspond to the fluorescence microscopy image within cell-laden hydrogels in the microfluidic device. The cells were stained by calcein AM (green) and Ethidium homodimer-1 (red). Green color and lack of red color signify high cell viability in the microgels. According to an embodiment, favorable results regarding for low-density cancer spheroid generation may be obtained with hydrogel compositions: 2-5 wt. % gelatin, and 0.5-1.5 wt. % a-CNC and any cell density between 100 to 1000 cells/µL. According to an embodiment, a preferred hydrogel composition is 2 wt. % gelatin and 0.75 wt. % a-CNC.

According to an embodiment, favorable results regarding for high-density cancer spheroid generation may be obtained with hydrogel compositions: 2-5 wt. % gelatin and 0.5-1 wt. % a-CNC and any cell density between $1\text{-}10\times10^7$ cells/mL. According to an embodiment, a preferred hydrogel composition is 2 wt. % gelatin and 0.5 wt. % a-CNC.

Physically-Crosslinked Hydrogel Scaffolds

According to an embodiment, any physically-crosslinked hydrogel scaffolds obtained via polymer chain interactions such as hydrophobic, electrostatic, and hydrogen bonding between polymer chains may be used as long as the hydrogel scaffolds have suitable characteristics, allow the formation and survival of multicellular aggregates and remain intact when subjected to continuous flows within the microfluidic device.

According to an embodiment, the hydrogel precursor may be a physically gelling polymer such as agarose. This embodiment is advantageous as the thermosetting gelation by which agarose forms hydrogels results in a fully formed hydrogel scaffold which is both non-cytotoxic and biocompatible. Furthermore, the use of agarose is also advantageous for this particular application as it may be readily functionalized with growth factors or peptide fragments to make the gel structures bioactive.

Figure 4A:
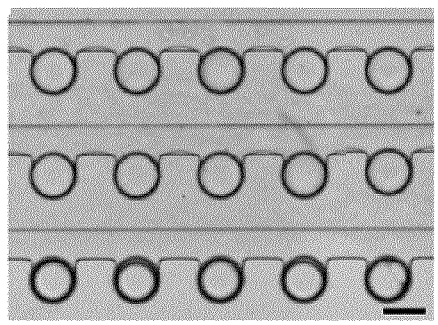
FIG. 4A shows a bright field image of the optimization of over swelling of cell-free agarose hydrogel spheroids.
Figure 4B:
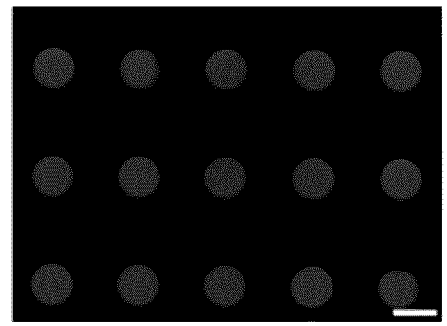
FIG. 4B shows a non-limiting example of fluorescence image of cell-free hydrogel spheroids using a hydrogel precursor with a polymer concentration of 1 wt. %.

According to an embodiment, when the precursor is agarose, the surface of the microwells and supplying channels may be treated with fluorinated oil (HFE 7500, 3M, Canada) mixed with 0.1 wt % block copolymer perfluorinated polyether-b-(polypropylene glycol-polyethylene glycol-polypropylene glycol)-b-perfluorinated polyether. In this particular embodiment of the cell encapsulation process a 0.1 wt % solution of PFPE-b-(PPG-PEGPPG)-b-PFPE in fluorinated oil is used. Next, the supplying channel and microwells may be filled with either an aqueous agarose solution or a cell suspension in an agarose solution therefore replacing the fluorinated oil mixture from the supplying channel and microwells. In the following step, the agarose solution or cell suspension in agarose solution in the supplying channel is replaced with a fluorination oil phase. Droplets of agarose solution are confined in the wells and cells are compartmentalized into the droplets. The temperature of the microfluidic device is then lowered to 4° C. to transform the droplets of agarose solution into gels. The resulting formations of such hydrogels are depicted in FIGS. 4A and 4B which show a bright field image and fluorescence image of cell-free agarose gels. After gelation, the oil phase in the supplying channel is replaced with a cell culture medium.

FIG. 18 shows spheroids formed from a high-density of MCF-7 cells laden in agarose microgels: FIG. 18A) droplets of high-density MCF-7 cell suspension (60%) in agarose solution at 37° C. [The droplets are suspended in fluorinated oil]. FIG. 18B) agarose microgels laden with MCF-7 cells (60%) in media after 1 day of cell culture.

Temperature-Responsive Hydrogels

According to an embodiment, the hydrogel scaffold may be a temperature-responsive hydrogel designed for 1) mimicking the structure and mechanical properties of in vivo tumor environments and allowing the growths of the multicellular cancer spheroids or organoids and 2) liquefying at a reduced, physiologically acceptable temperature for the subsequent release of the spheroids or organoids from the MF device.

According to an embodiment, the hydrogel precursor may be derived from cellulose nanocrystals (CNCs). For example, the hydrogel precursor may be an aqueous suspension of CNCs surface-functionalized with temperature-responsive polymer molecules. In non-limiting examples, such modified CNCs may be CNCs carrying surface-grafted molecules of the temperature-responsive polymer poly(N-isopropylacrylamide) (Li, Y. et al., Angew Chem Int Ed Engl (2017)56(22):6083-6087 entitled Supramolecular Nanofibrillar Thermoreversible Hydrogel for Growth and Release of Cancer Spheroids; Li, Y. and Kumacheva, E., Science Advances (2018) 4(4):eaas8998 entitled Hydrogel microenvironments for cancer spheroid growth and drug screening) or CNCs functionalized with a copolymer of N-isopropylacrylamide and N,N'-dimethylaminoethyl methacrylate (Thérien-Aubin, H., et al., Biomacromolecules (2016) 17(10):3244-3251 entitled Temperature-Responsive Nanofibrillar Hydrogels for Cell Encapsulation).

Application of MF-MSF Platform for Screening

According to an embodiment, the device and method may be used for screening compounds for drug discovery, for understanding mode of action of the screened compounds and for the evaluation of pharmacodynamics and/or mechanistic biomarkers. According to an embodiment, the device and method may be particularly useful in the screening of drug efficacy for therapeutic treatment by delivering drugs such as anticancer drugs to multicellular spheroids or organoids under dynamic conditions. According to an embodiment, the anticancer drugs may target breast cancer or pancreatic cancer. One advantage of the present invention is the use of multicellular spheroids obtained from primary cells isolated from cancer patient tissue rendering possible a personalized screening of compounds.

According to an embodiment, a method for screening compounds using the microfluidic device 10 of the present disclosure. The method may comprise the steps of 1) introducing a first wetting agent 25a into the supplying channel 14 and corresponding microwells 16 of at least one row of the microfluidic device 10;

2) introducing a solution 21 comprising an aqueous suspension of cells 23 and an hydrogel precursor 22 into the supplying channel 14 and corresponding microwells 16 of the at least one row 50 of the microfluidic device 10 to displace the first wetting agent 25a within the supplying channel 14 and the microwells 16 with the solution 21;

3) introducing a second wetting agent 25b into the supplying channel 14 of the at least one row 50 of the microfluidic device 10 to displace the solution 21 within the supplying channel 14 with the second wetting agent 25b, wherein displace the solution 21 in the supplying channel 14 with the second wetting agent 25b induces the formation of droplets 24 containing the aqueous suspension of cells 23 and the hydrogel precursor 22 within the microwells 16 of the at least one row 50 of the microfluidic device 10;

4) inducing the gelation of the hydrogel precursor 22 within the droplets 24 to form a hydrogel 27 seeded with the suspension of cells 23 within the microwells 16;

5) introducing one or more cell culture mediums 26 into the supplying channel 14 of the at least one row 50 of the microfluidic device 10 to displace the second wetting agent 25b in the supplying channel 14;

6) continuously flowing the one or more cell culture mediums 26 into the supplying channel 14 of the at least one row 50 of the microfluidic device 10, wherein the cell culture medium(s) 26 promotes cell growth of the suspension of cells 23 and the formation of the multicellular aggregates 26 within the hydrogels 27;

7) exposing selected multicellular aggregates 26 to a compound by introducing a solution comprising the compound into at least one of the supplying channel for a period of time; and 8) assessing the viability of the multicellular aggregates 26 exposed to the compound.

According to a non-limiting embodiment, the screened compound may be a drug, protein, hormone, antibody, nanoparticle or a toxin.

According to an embodiment, the screening method may be used with multicellular spheroids obtained from different cancer cells and the compound is an anticancer drug. Furthermore, the multicellular spheroids may be obtained from breast cancer and the anticancer drug targets breast cancer.

Alternatively, the multicellular spheroids may be obtained from pancreatic cancer and the anticancer drug targets pancreatic cancer According to an embodiment, the MCCs may be obtained from primary cells isolated from cancer patient tissue for a personalized screening of compounds.

According to an embodiment, the multicellular spheroids may be obtained with the use of a solution comprising the aqueous suspension of cells having a plurality of different types of cells.

The method of the present disclosure provides the opportunity of screening a plurality of compounds on the microfluidic device. Furthermore, the present invention also provides the opportunity of screening a plurality of concentrations for each screened compound. According to an embodiment, solutions of individual drugs supplied in different doses or drug combinations may be supplied with a nutrition medium to the multicellular spheroids located in different rows 50.

According to an embodiment, the screening may be performed on multicellular spheroids of different dimensions on the same microfluidic device.

Penetration of the Dye in Polymer-MCS under Flow

According to an embodiment, the device and method may be used for screening compounds for drug discovery, for understanding mode of action of the screened compounds and for the evaluation of pharmacodynamics and/or mechanistic biomarkers.

According to an embodiment, the device and method may be particularly useful in the study and/or screening of drugs for therapeutic treatment by delivering drugs such as anticancer drugs to multicellular spheroids or organoids obtained either from high-density cell suspensions or low-density cell suspensions, under dynamic conditions.

Figure 27:
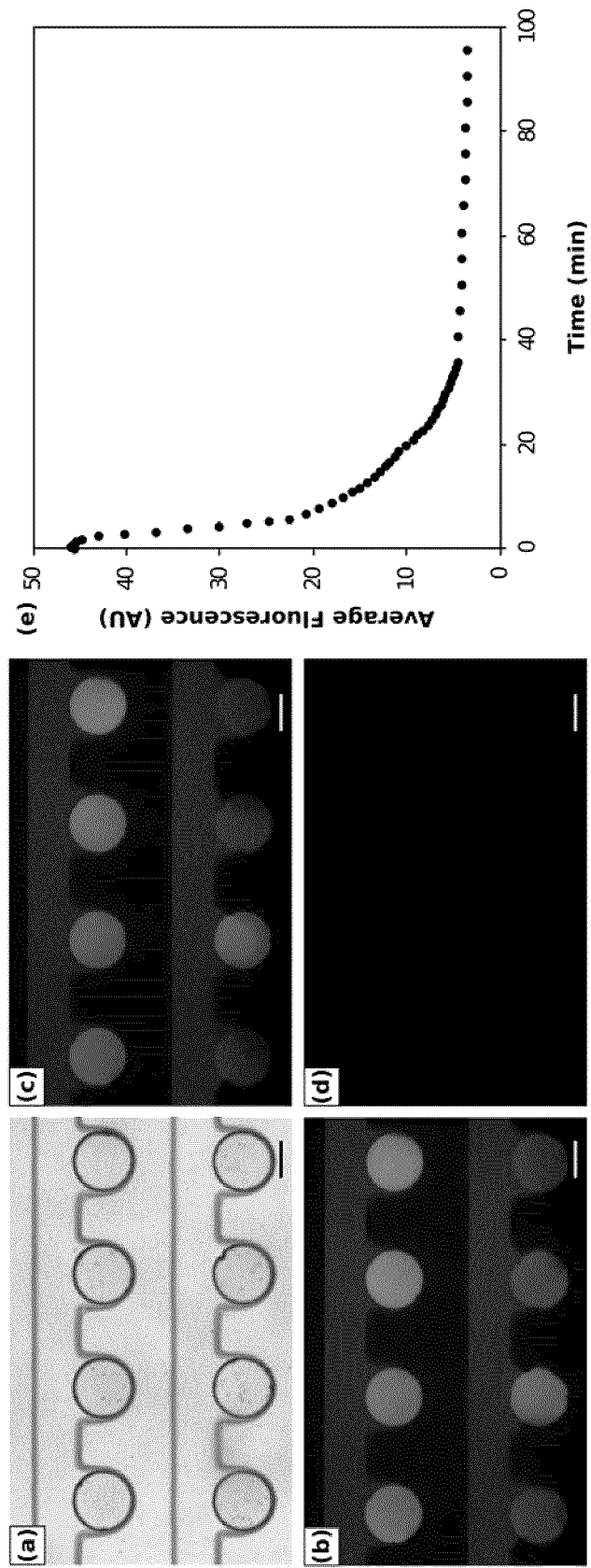
FIG. 27 shows the penetration of FITC-dextran within a-CNC/gelatin microgels with multi-cellular spheroids; (a)

In an additional non-limiting example, to demonstrate the use of the method and system of the present invention for studying and/or screening the effects of compounds on the spheroids or organoids, a fluorescent dye Fluorescein isothiocyanate-dextran (FITC-dextran) with hydrodynamic diameter of 12 nm was used to characterize the permeability of multi-cellular spheroids. Before the introduction of FITC-dextran solution, a 2D array of a-CNC/gelatin microgels with multi-cellular spheroids with a cell concentration of $1.2 \times 10^8$ cell/mL was formed in the microfluidic device and cultured under the flow rate of the medium at 0.01 mL/h for 3 days (FIG. 27*a*). Then, a solution of 0.1 mg/mL FITC-dextran in HBSS was infused into the a-CNC/gelatin microgels with multi-cellular spheroids at a flow rate of 0.1 mL/h. After a perfusion time, t, of 10 min, the channels and contents of wells became fluorescent. After a perfusion time of 30 min, the fluorescence intensity of the supplying microchannel and well contents did not change, anymore (FIG. 27*b*). After that, a dye-free cell culture medium was infused into the channels at a flow rate of 0.1 mL/h. FIG. 27*c* shows the microgels after 10 s or perfusion. After short perfusion time (t') of 10 min, the fluorescent intensity in the supplying channels noticeably decreased. The fluorescence intensity of the a-CNC/gelatin microgels with multi-cellular spheroids also reduced. After 80 min perfusion, the fluorescence intensity of the FITC-dextran in the a-CNC/gelatin microgels with multi-cellular spheroids very significantly diminished (FIG. 27*d*).

The decrease in the mean fluorescence intensity of FITC-dextran in the a-CNC/gelatin microgels with multi-cellular spheroids was quantified as a function of washing time (FIG. 27*f*). The fluorescence intensity dramatically (~80%) reduced after the first 20 min washing and then it slowly (~10%) reduced during subsequent 50 min, remaining almost constant after t=60 min.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method for producing multicellular aggregates, in a microfluidic device comprising at least one row having at least one microwell, for each row, a supplying channel spanning along a length of the row and each microwell is in flow connection with the supplying channel, the method comprising the steps of:

introducing a first wetting agent into the supplying channel and corresponding microwells of at least one row of the microfluidic device;

introducing a solution comprising an aqueous suspension of cells and a hydrogel precursor into the supplying channel and corresponding at least one microwell of the at least one row of the microfluidic device to replace the first wetting agent within the supplying channel and the at least one microwell with the solution;

introducing a second wetting agent into the supplying channel of the at least one row of the microfluidic device to replace the solution within the supplying channel with the second wetting agent, wherein replacing the solution in the supplying channel with the second wetting agent induces the formation of droplets containing the aqueous suspension of cells and the hydrogel precursor within the at least one microwell of the at least one row of the microfluidic device, wherein the formation of the droplets is confined in the microwell;

inducing the gelation of the hydrogel precursor within the droplets to form a hydrogel seeded with the suspension of cells; and introducing a cell culture medium into the supplying channel of the at least one row of the microfluidic device to replace the second wetting agent in the supplying channel, to form multicellular aggregates within the hydrogel.

2. The method of claim 1 further comprising the step of continuously flowing the cell culture medium into the supplying channel of the at least one row of the microfluidic device, wherein the cell culture medium promotes cell growth of the suspension of cells and the formation of the multicellular aggregates within the hydrogels.

3. The method of claim 1 wherein the first wetting agent and the second wetting agent are the same.

4. The method of claim 1 wherein the hydrogel precursor comprises a synthetic monomer or polymer, a biopolymer or a combination thereof.

5. The method of claim 1 wherein the gelation of the hydrogels occurs within at least 10 min, about 30 minutes to 1.5 hours or about 1 to about 1.5 hours.

6. The method of claim 1 wherein the multicellular aggregates are multicellular spheroids.

7. The method of claim 1 wherein the hydrogels containing the multicellular aggregates have a stiffness ranging between about 10 Pa to hundreds kPa or 50 Pa to about 100 KPa or 10 Pa to about 20 KPa.

8. The method of claim 2 wherein the hydrogels containing the multicellular aggregates are released from the microwells into the supplying channel and moved to the corresponding supplying exit for retrieval of the hydrogels from the microfluidic device.

9. The method of claim 1 wherein the solution comprises the aqueous suspension of cells comprising a plurality of different types of cells.

10. The method of claim 1, wherein the hydrogel precursor comprises a temperature-responsive polymer.

11. A method for compound screening with multicellular aggregates in a microfluidic device comprising at least one row having a plurality of microwells, for each row, a supplying channel spanning along a length of the row and each microwell is in flow connection with the supplying channel, the method comprising the steps of:
- introducing a first wetting agent into the supplying channel and corresponding microwells of at least one row of the microfluidic device;
- introducing a solution comprising an aqueous suspension of cells and an hydrogel precursor into the supplying channel and corresponding microwells of the at least one row of the microfluidic device to replace the first wetting agent within the supplying channel and the microwells with the solution;
- introducing a second wetting agent into the supplying channel of the at least one row of the microfluidic device to replace the solution within the supplying channel with the second wetting agent, wherein replacing the solution in the supplying channel with the second wetting agent induces the formation of droplets containing the aqueous suspension of cells and the hydrogel precursor within the microwells of the at least one row of the microfluidic device, wherein the formation of the droplets is confined in the microwell;
- inducing the gelation of the hydrogel precursor within the droplets to form a hydrogel seeded with the suspension of cells;
- introducing a cell culture medium into the supplying channel of the at least one row of the microfluidic device to replace the second wetting agent in the supplying channel;
- continuously flowing the cell culture medium into the supplying channel of the at least one row of the microfluidic device, wherein the cell culture medium promotes cell growth of the suspension of cells and the formation of the multicellular aggregates within the hydrogels;
- exposing selected multicellular aggregates to a compound by introducing a solution comprising the compound into at least one of the supplying channel for a period of time; and
- assessing the viability of the multicellular aggregates exposed to the compound.

12. The method of claim 11 wherein the compound is a drug.

13. The method of claim 11 wherein the multicellular aggregates are multicellular cancer spheroids obtained from primary cells isolated from cancer patient tissue.

\* \* \* \* \*